United States Patent
Balch et al.

(10) Patent No.: US 12,049,658 B2
(45) Date of Patent: *Jul. 30, 2024

(54) PRODUCTION OF RETINYL ESTERS

(71) Applicant: DSM IP ASSETS B.V., Heerlen (NL)

(72) Inventors: Nathalie Balch, Kaiseraugst (CH); Paul Blomquist, Kaiseraugst (CH); Reed Doten, Kaiseraugst (CH); Peter Houston, Kaiseraugst (CH); Ethan Lam, Kaiseraugst (CH); Jenna Mcmahon, Kaiseraugst (CH); Joshua Trueheart, Kaiseraugst (CH); Celine Viarouge, Kaiseraugst (CH); René Marcel De Jong, Kaiseraugst (CH)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/648,879

(22) PCT Filed: Sep. 25, 2018

(86) PCT No.: PCT/EP2018/076034
§ 371 (c)(1),
(2) Date: Mar. 19, 2020

(87) PCT Pub. No.: WO2019/058001
PCT Pub. Date: Mar. 28, 2019

(65) Prior Publication Data
US 2020/0239925 A1    Jul. 30, 2020

Related U.S. Application Data

(60) Provisional application No. 62/562,672, filed on Sep. 25, 2017.

(30) Foreign Application Priority Data

Apr. 20, 2018   (EP) ..................... 18168564

(51) Int. Cl.
C12P 23/00    (2006.01)
(52) U.S. Cl.
CPC ................... *C12P 23/00* (2013.01)
(58) Field of Classification Search
CPC .................................... C12P 23/00
See application file for complete search history.

(56) References Cited

U.S. PATENT DOCUMENTS

2014/0170720 A1    6/2014  Kim et al.
2015/0322412 A1*  11/2015  Farrell ............... C12P 23/00
                                                    435/67
2016/0130628 A1    5/2016  Kim

FOREIGN PATENT DOCUMENTS

WO         2014/096992        6/2014
WO        2014096992 A1       6/2014
WO     WO-2014096992 A1 *     6/2014  ........... C12N 9/1029

OTHER PUBLICATIONS

Jang HJ, Ha BK, Zhou J, Ahn J, Yoon SH, Kim SW. Selective retinol production by modulating the composition of retinoids from metabolically engineered E. coli. Biotechnol Bioeng. Aug. 2015;112(8):1604-12. doi: 10.1002/bit.25577. Epub May 12, 2015. PMID: 25726762. (Year: 2015).*
Verstrepen KJ, Van Laere SD, Vanderhaegen BM, Derdelinckx G, Dufour JP, Pretorius IS, Winderickx J, Thevelein JM, Delvaux FR . Expression levels of the yeast alcohol acetyltransferase genes ATF1, Lg-ATF1, and ATF2 control the formation of a broad range of volatile esters. 2003 (Year: 2003).*
Akacha, N. B., & Gargouri, M. (2015). Microbial and enzymatic technologies used for the production of natural aroma compounds: Synthesis, recovery modeling, and bioprocesses. Food and Bioproducts Processing, 94, 675-706. (Year: 2015).*
International Search Report for PCT/EP2018/076034, mailed Nov. 13, 2018, 5 pages.
Written Opinion of the ISA for PCT/EP2018/076034, mailed Nov. 13, 2018, 7 pages.
Ding et al., "The Yeast ATF1 Acetyltransferase Efficiently Acetylates Insect Pheromone Alcohols: Implications for the Biological Production of Moth Pheromones", Lipids (2016) vol. 51, pp. 469-475.
Jang et al., "Selective Retinol Production by Modulating the Composition of Retinoids from Metabolically Engineered *E. coli*", Biotechnology and Bioengineering, vol. 112, No. 8, (2025); 10 pages.
Verstrepen et al., "Expression Levels of the Yeast Alcohol Acetyltransferase Genes ATF1, Lg-ATF1, and ATF2 Control the Formation of a Broad Range of Volatile Esters", Applied and Environmental Microbiology, pp. 5228-5237 (2003).
Akacha et al., "Microbial and enzymatic technologies used for the (I) CrMark production of natural aroma compounds: Synthesis, recovery modeling, and bioprocesses", Food and Bioproducts Processing, pp. 675-706 (2015).

* cited by examiner

*Primary Examiner* — Robert J Yamasaki
*Assistant Examiner* — Trevor Kane
(74) *Attorney, Agent, or Firm* — Nixon & Vanderhye, PC

(57)   ABSTRACT

The present invention is related to production of retinyl esters, such as in particular retinyl acetate, an important building block for production of vitamin A. The retinyl esters might be generated via enzymatic conversion of retinol which process includes the use of enzymes with acetyl-transferase (ATF) activity, thus acetylating retinol into retinol/retinyl acetate. Said process is particularly useful for biotechnological production of vitamin A.

4 Claims, No Drawings

Specification includes a Sequence Listing.

SEQUENCE LISTING

```
<160> NUMBER OF SEQ ID NOS: 19

<210> SEQ ID NO 1
<211> LENGTH: 525
<212> TYPE: PRT
<213> ORGANISM: Saccharomyces bayanus

<400> SEQUENCE: 1

Met Asn Thr Tyr Ser Glu Lys Thr Ser Leu Val Gln Asp Glu Cys Leu
1               5                   10                  15

Ala Lys Met Ile Gln Asn Gly His Ser Arg Arg Met Gly Ser Val Glu
            20                  25                  30

Asp Leu Tyr Ala Ala Leu Asn Arg Gln Lys Leu Tyr Arg Asn Phe Ser
        35                  40                  45

Thr Tyr Ser Glu Leu Asn Asp Tyr Cys Thr Lys Asp Gln Leu Ala Leu
    50                  55                  60

Ala Leu Arg Asn Ile Cys Leu Lys Asn Pro Thr Leu Leu His Ile Val
65                  70                  75                  80

Leu Pro Ala Arg Trp Pro Asp His Glu Asn Tyr Tyr Leu Ser Ser Glu
                85                  90                  95

Tyr Tyr Ser Gln Pro His Pro Lys His Asp Tyr Ile Ser Val Leu Pro
            100                 105                 110

Glu Leu Lys Phe Asp Gly Val Ile Leu Asn Glu Gln Pro Glu His Asn
        115                 120                 125

Ala Leu Met Lys Gln Ile Leu Glu Glu Leu Lys Asp Ser Asn Gly Ser
    130                 135                 140

Tyr Thr Ala Lys Ile Phe Lys Leu Thr Thr Ala Leu Thr Ile Pro Tyr
145                 150                 155                 160

Ala Gly Pro Thr Ser Pro Thr Trp Arg Leu Ile Cys Leu Pro Glu Glu
                165                 170                 175

Gly Tyr Thr Asp Lys Trp Lys Phe Ile Phe Leu Ser Asn His Cys
            180                 185                 190

Met Cys Asp Gly Arg Thr Ser Ile His Phe Phe Gln Asp Leu Arg Asp
    195                 200                 205

Glu Leu Asn Asn Ile Lys Thr Pro Pro Lys Lys Leu Asp Tyr Ile Phe
    210                 215                 220

Gln Tyr Glu Lys Asp Tyr Gln Leu Leu Arg Lys Leu Pro Glu Pro Ile
225                 230                 235                 240

Glu Asn Met Ile Asp Phe Arg Pro Pro Tyr Met Phe Ile Pro Lys Ser
                245                 250                 255

Leu Ile Ser Gly Phe Ile Tyr Ser His Leu Arg Phe Ser Ser Lys Gly
            260                 265                 270

Val Cys Thr Arg Met Asp Glu Leu Glu Lys Asn Asp Asp Ile Val Thr
        275                 280                 285

Glu Ile Ile Thr Ile Ser Pro Ser Glu Leu Gln Lys Ile Arg Thr Lys
    290                 295                 300
```

Ile Lys Ser Asn Ile Pro Gly Lys Cys Thr Ile Thr Pro Phe Leu Glu
305                 310                 315                 320

Val Cys Trp Phe Val Ser Leu His Lys Trp Gly Lys Phe Lys Pro
        325                 330                 335

Leu Lys Phe Glu Trp Leu Thr Asp Val Phe Ile Pro Ala Asp Cys Arg
            340                 345                 350

Ser Leu Leu Pro Glu Asp Glu Asp Val Arg Ala Met Tyr Arg Tyr Gly
        355                 360                 365

Ala Asn Val Gly Phe Val Asp Phe Thr Pro Trp Ile Ser Glu Phe Asn
    370                 375                 380

Met Asn Asp Ser Lys Glu Asn Phe Trp Pro Leu Ile Ala His Tyr His
385                 390                 395                 400

Glu Val Ile Ser Gly Ala Ile Asn Asp Lys Lys His Leu Asn Gly Leu
                405                 410                 415

Gly Phe Asn Ile Gln Gly Leu Val Gln Lys Tyr Val Asn Ile Asp Lys
            420                 425                 430

Val Met Arg Asp Arg Ala Leu Gly Lys Ser Arg Gly Gly Thr Leu Leu
        435                 440                 445

Ser Asn Val Gly Ile Phe His Gln Ser Glu Glu Thr Asp Ser Arg Tyr
    450                 455                 460

Ser Ile Arg Asp Leu Ala Phe Gly Gln Phe Gln Gly Ser Trp His Gln
465                 470                 475                 480

Ala Phe Ser Leu Gly Val Cys Ser Thr Asn Val Lys Gly Met Asn Ile
                485                 490                 495

Val Ile Ser Ser Thr Lys Asn Ala Val Gly Ser Gln Glu Leu Leu Glu
            500                 505                 510

Glu Leu Cys Ala Met Tyr Lys Ala Leu Leu Leu Asp Pro
        515                 520                 525

<210> SEQ ID NO 2
<211> LENGTH: 1578
<212> TYPE: DNA
<213> ORGANISM: Artificial Sequence
<220> FEATURE:
<223> OTHER INFORMATION: Yarrowia codon-optimized SbATF1

<400> SEQUENCE: 2

```
atgaacacct actctgagaa gacctctctt gttcaggacg agtgtctggc taagatgatt      60
cagaacggtc actctcgacg aatgggctct gtcgaggacc tttacgccgc cctcaaccga     120
cagaagctct accgaaactt ctctacttac tctgagctga acgattactg cactaaggat     180
cagctcgctc ttgctctccg aaacatttgt ctgaagaacc ccactctcct tcacattgtt     240
cttcccgctc gatggcccga tcacgagaac tactaccttt cttctgagta ctactctcag     300
ccccacccca agcacgatta catctctgtt cttcccgagc tgaagttcga tggtgtgatt     360
ctcaacgagc agcccgagca aacgcccctt atgaagcaga ttcttgagga gcttaaggat     420
tccaacggtt cttacactgc taagattttc aagctcacta ccgctctcac tattccctac     480
gctggtccca cttctcccac ttggcgactg atttgtctgc cgaggaggg atacaccgat     540 aagtggaaga agtttatttt cctttccaac cactgcatgt gtgatggtcg aacctctatt     600
cacttctttc aggatctccg agatgagctt aacaacatca agactccccc caagaagctc     660
gactacattt ccagtacgga gaaggactac cagcttctcc gaaagctccc cgagcccatt     720
gagaacatga ttgattttcg accccctac atgtttattc ccaagtccct tatttccggc     780
```

```
ttcatttact cccaccttcg attctcctct aagggtgtgt gtacccgaat ggacgagctt    840
gagaagaacg acgatattgt tactgagatc atcaccatct ctccctctga gcttcagaag    900
attcgaacta agatcaagtc taacattccc ggcaagtgca ccatcactcc cttccttgag    960
gtttgttggt tgtttctct ccacaagtgg ggcaagtttt tcaagcccct caagttcgag   1020
tggcttaccg atgtttttat tcccgctgat tgccgatctc tgctccccga ggacgaggac   1080
gtgcgagcta tgtaccgata cggcgctaac gtcggttttg ttgacttcac tccctggatt   1140
tctgagttta acatgaacga ctctaaggag aacttctggc cccttattgc tcactaccac   1200
gaggttattt ctggtgccat caacgacaag aagcacctca acggtcttgg tttcaacatt   1260
cagggccttg tccagaagta cgtcaacatt gacaaggtga tgcgagatcg agcccttggt   1320
aagtcccgag gaggcaccct gctctctaac gtgggtattt tccaccagtc tgaggagact   1380
gactcccgat actctatccg agacctcgct ttcggtcagt tcagggttc ttggcaccag   1440 gctttctctc tcggtgtttg ttccactaac gtgaagggaa tgaacattgt tatttcttcc   1500
actaagaacg ccgtgggttc ccaggagctc cttgaggagc tttgtgccat gtacaaggct   1560
ctgctccttg accctaa                                                  1578

<210> SEQ ID NO 3
<211> LENGTH: 391
<212> TYPE: PRT
<213> ORGANISM: Fragaria x ananassa

<400> SEQUENCE: 3

Met Ser Tyr Lys Asn Asn His Ser Ile Leu Ser Lys Pro Asn Asp Pro
1               5                   10                  15

Val Glu Val Ile Arg Asp Ala Leu Ser Lys Ala Leu Gln Phe Tyr Tyr
                20                  25                  30

Pro Leu Ala Gly Arg Leu Arg Glu Gly Pro Asn Lys Lys Leu Met Val
            35                  40                  45

Asp Cys Thr Gly Glu Gly Ile Leu Phe Val Glu Ala Asn Ala Glu Val
        50                  55                  60

Thr Leu Asp Glu Leu Gly Asp Ala Ile Leu Pro Pro Cys Pro Phe Leu
65                  70                  75                  80

Asp Gly Phe Leu Phe Asn Val Pro Gly Ser Asp Gly Ile Leu Gly Ser
                85                  90                  95

Pro Leu Cys Leu Ile Gln Val Thr Arg Leu Ser Cys Gly Gly Phe Ile
            100                 105                 110

Phe Ala Leu Arg Leu Asn His Thr Ile Cys Asp Ala Leu Gly Leu Val
            115                 120                 125

Gln Phe Leu Asn Ala Val Gly Glu Ile Ala Gln Gly Lys Tyr Ala Pro
        130                 135                 140

Ser Ile Thr Pro Val Trp Glu Arg Glu Leu Leu Ser Ala Arg Asp Pro
145                 150                 155                 160

Pro Arg Ile Ser Cys Thr His Glu Glu Phe Asp Ser Ile Asp His
                165                 170                 175

Ser Tyr Pro Asn Tyr Gly Ala Thr Val Gln Gln Cys Tyr Cys Phe Gly
            180                 185                 190

Pro Lys Glu Ile Lys Ser Leu Arg Glu His Leu Pro Pro His Leu Ser
            195                 200                 205

Thr Cys Ser Ser Thr Phe Glu Leu Ile Thr Ala Cys Val Trp Lys Cys
        210                 215                 220

Arg Thr Ile Ser Leu Asp Met Asp Pro Glu Gln Ile Val Arg Leu Ser
```

```
            225                 230                 235                 240
Cys Val Val Thr Ala Leu Gly Lys His Asn Asn Val Cys Leu Pro Leu
                245                 250                 255

Gly Tyr Tyr Gly Asn Thr Phe Thr Tyr Pro Ala Val Val Ser Thr Ala
                260                 265                 270

Glu Arg Leu Cys Asn Ser Pro Leu Gly Tyr Ala Val Glu Leu Val Lys
                275                 280                 285

Lys Ser Lys Ala Lys Met Ser Glu Glu Tyr Leu Arg Ser Ala Ile Asp
290                 295                 300

Phe Val Glu Val Arg Gly Arg Pro Pro Phe Ala Leu Glu Gly Met Ser
305                 310                 315                 320

Asp Phe Leu Val Ser Asp Asn Thr Arg Thr Gly Leu Gly Glu Ile Asp
                325                 330                 335

Phe Gly Phe Gly Lys Pro Val Tyr Ala Gly Val Ala Lys Ser Thr Asp
                340                 345                 350

Leu Ile Ser Phe Tyr Val Arg Ser Thr Asn Lys Glu Glu Arg Glu Ile
                355                 360                 365

Leu Val Pro Val Cys Leu Pro Ile Leu Ser Met Glu Ile Phe Gln Gln
                370                 375                 380

Glu Leu Lys Lys Met Ile Gly
385                 390

<210> SEQ ID NO 4
<211> LENGTH: 1176
<212> TYPE: DNA
<213> ORGANISM: Artificial Sequence
<220> FEATURE:
<223> OTHER INFORMATION: Yarrowia codon-optimized FaATF

<400> SEQUENCE: 4
atgtcttaca agaacaacca ctctattctg tctaagccta acgaccctgt cgaggtgatt      60
cgagatgccc tgtccaaggc ccttcagttt tactaccctc tcgctggacg actccgagag     120
ggtcccaaca gaagctcat ggtggactgc actggtgagg aatcctctt gttgaggct        180 aacgctgagg tcactctcga tgagctcggc gatgctatcc ttccccctg tccttttctt     240 gacggttttc tctttaacgt gcccggttct gacggtattc ttggttctcc tctctgtctt     300
attcaggtca ctcgactctc ttgtggaggt tttattttg ctctgcgact taaccacact     360
atttgcgatg ctctgggtct tgttcagttt ctcaacgctg ttggcgagat tgcccaggga    420
aagtacgctc cttctattac ccctgtttgg gagcgagagc tcctctctgc ccgagaccct    480
ccccgaattt cctgtactca cgaggagttt gacgattcta ttgaccactc ttaccctaac    540
tacggtgcta ccgttcagca gtgttactgt tttggtccca aggagatcaa gtcccttcga    600
gagcaccttc cccctcacct ttctacttgt tcttccactt tcgagcttat tactgcttgt    660
gtgtggaagt gccgaactat ctctctcgat atggaccctg agcagattgt ccgactctct    720
tgcgttgtta ctgctcttgg taagcacaac aacgtttgtc ccctctcgg atactacgga    780 aacactttca cttaccctgc tgttgtttct actgccgagc gactttgtaa ctctcccctg    840
ggttacgctg tggagcttgt caagaagtcc aaggctaaga tgtctgagga gtaccttcga    900
tctgctattg actttgtcga ggttcgagga cgaccccct tgctcttga gggtatgtct    960 gacttccttg tttccgataa cactcgaact ggtcttggtg agattgactt tggcttcgga    1020
aagcctgttt acgctggagt tgccaagtcc accgatctca tctccttta cgtccgatcc    1080 actaacaagg aggagcgaga gattcttgtc cctgtttgcc ttcccattct gtctatggag    1140
```
atttttcagc aggagctcaa gaagatgatt ggttaa       1176

<210> SEQ ID NO 5
<211> LENGTH: 219
<212> TYPE: PRT
<213> ORGANISM: Escherichia coli

<400> SEQUENCE: 5

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 6
<211> LENGTH: 660
<212> TYPE: DNA
<213> ORGANISM: Artificial Sequence
<220> FEATURE:
<223> OTHER INFORMATION: Yarrowia codon-optimized EcCAT

<400> SEQUENCE: 6
atggagaaga agattactgg ttacaccact gtcgatattt ctcagtggca ccgaaaggag      60
cactttgagg cttttcagtc tgttgctcag tgtacttaca accagaccgt tcagctcgat     120
attaccgctt tccttaagac tgtcaagaag aacaagcaca gttttacccc tgcctttatt     180
cacattcttg cccgactgat gaacgctcac cctgagttcc gaatggctat gaaggatggt     240
gagctcgtga tttgggattc tgttcaccct tgttacaccg tttttcacga gcagactgag     300
actttctctt ccctctggtc tgagtaccac gatgacttcc gacagttcct tcacatttac     360
tctcaggatg tcgcctgtta cggtgagaac ctggcttact cccctaaggg ttttattgag     420
aacatgtttt tcgtgtctgc taaccccctgg gtttccttca cctcttttga ccttaacgtg     480

```
gctaacatgg acaacttctt cgcccccgtt ttcactatgg gaaagtacta cactcagggc      540
gacaaggtgc tcatgcccct ggccattcag gttcaccacg ctgtctgtga tggctttcac      600
gtcggtcgaa tgcttaacga gcttcagcag tactgcgatg agtggcaggg cggcgcttag      660
```

<210> SEQ ID NO 7
<211> LENGTH: 363
<212> TYPE: PRT
<213> ORGANISM: Euonymus alatus

<400> SEQUENCE: 7

```
Met Met Asp Ala His Gln Glu Ile Lys Asn Phe Ile Lys Val Trp Val
1               5                   10                  15

Gln Ala Met Val Cys Leu Ser Tyr Ala Tyr Tyr Phe Ser Ser Arg Leu
                20                  25                  30

Pro Lys Gly Leu Leu Arg Leu Leu Ser Leu Pro Val Leu Tyr Leu
            35                  40                  45

Leu Leu Ile Ala Pro Leu Asn Ile Ser Ser Phe Ile Leu Ser Ser Ile
50                  55                  60

Thr Gly Phe Phe Leu Ala Trp Leu Thr Thr Phe Lys Val Ile Ser Phe
65                  70                  75                  80

Ala Phe Asp Gln Gly Pro Leu Tyr Pro Leu Pro Gln Asn Leu Leu His
                85                  90                  95

Phe Ile Ser Ile Ala Cys Leu Pro Ile Thr Ile Lys Arg Asn Pro Ser
            100                 105                 110

Pro Lys Leu Lys Ser Thr Thr Asn Pro Ser Pro Ile Ser His Leu Leu
        115                 120                 125

Lys Lys Ala Phe Met Ser Phe Pro Ser Lys Val Leu Phe His Trp Val
130                 135                 140

Ile Ala His Leu Tyr Gln Tyr Lys Lys Tyr Met Asp Pro Asn Val Val
145                 150                 155                 160

Leu Val Ile Tyr Cys Cys His Val Tyr Val Met Leu Asp Ile Ser Leu
                165                 170                 175

Ser Leu Cys Ala Thr Leu Ala Glu Phe Leu Cys Gly Phe Asp Val Glu
            180                 185                 190

Pro Gln Phe Lys Glu Pro Tyr Leu Ala Thr Ser Leu Gln Asp Phe Trp
        195                 200                 205

Gly Arg Arg Trp Asn Ile Ile Val Ser Ser Val Leu Arg Ser Thr Val
210                 215                 220

Tyr Ala Pro Thr Arg Asn Ile Ala Ser Tyr Leu Ile Gly Ser Arg Trp
225                 230                 235                 240

Ala Tyr Phe Pro Ala Ile Ile Ala Thr Phe Val Val Ser Gly Val Met
                245                 250                 255

His Asp Val Val Tyr Tyr Val Tyr Met Met His Met Tyr Pro Lys Trp
            260                 265                 270

Asp Met Thr Gly His Phe Val Leu His Gly Ile Cys Glu Ala Leu Glu
        275                 280                 285

Val Glu Met Lys Cys Lys Arg Ser Arg Ser Asp Lys Trp Arg Arg His
290                 295                 300

Pro Ala Val Asp Trp Val Met Val Met Gly Phe Val Met Gly Thr Ser
305                 310                 315                 320

Val Ser Leu Leu Phe Val Pro Leu Leu Arg Asp Asn Val Asp Gln Ile
                325                 330                 335

Val Ala Glu Glu Tyr Ser Ile Leu Phe Asn Phe Val Arg Glu Lys Ile
            340                 345                 350
```

Val Met Leu Gly Thr Arg Phe Val Cys Gly Asn
        355                 360

<210> SEQ ID NO 8
<211> LENGTH: 1092
<212> TYPE: DNA
<213> ORGANISM: Artificial Sequence
<220> FEATURE:
<223> OTHER INFORMATION: Yarrowia codon-optimized EaCAcT

<400> SEQUENCE: 8

```
atgatggatg ctcaccagga gatcaagaac ttcatcaagg tttgggtgca ggctatggtg      60
tgtctttctt acgcttacta cttctcctct cgacttccca agggactcct tcgacttctc     120
tctcttctcc ctgttcttta ccttctcctt atcgctcccc ttaacatttc ctctttcatt     180
cttcttccta tcaccggctt cttccttgct tggcttacca ctttcaaggt catctctttt     240
gctttcgatc agggtcctct ctaccctctc cctcagaacc tccttcactt catttccatt     300
gcttgtctcc ctatcactat caagcgaaac ccctctccta agctcaagtc caccactaac     360
ccttctccta tttctcacct tctcaagaag gcttttatgt cttttccctc taaggttctt     420
ttccactggg tcattgctca cctttaccag tacaagaagt acatggaccc taacgtggtc     480
ctcgttatct actgttgtca cgtttacgtt atgcttgaca tttctctctc tctgtgtgct     540
accctggctg agtttctctg tggttttgac gttgagcctc agtttaagga gccttacctt     600
gctacttctc ttcaggactt tggggccga cgatggaaca ttattgtctc ttctgtcctg     660
cgatccactg tttacgctcc cactcgaaac attgcttctt accttattgg atctcgatgg     720
gcttactttc ccgctattat tgctactttc gttgtgtctg gagttatgca cgatgtcgtg     780
tactacgttt acatgatgca catgtaccct aagtgggata tgactggtca cttcgtcctt     840
cacggaattt gtgaggctct ggaggtggag atgaagtgta agcgatctcg atctgacaag     900
tggcgacgac accctgctgt cgattgggtg atggtgatgg ttttgtcat gggtacttct     960
gtttccctcc ttttcgtccc ctccttcga gataacgtcg atcagattgt tgctgaggag    1020
tactctattc tctttaactt tgttcgagag aagattgtca tgcttggtac tcgatttgtc    1080
tgtggaaact aa                                                        1092
```

<210> SEQ ID NO 9
<211> LENGTH: 459
<212> TYPE: PRT
<213> ORGANISM: Malus domestica

<400> SEQUENCE: 9

Met Met Pro Phe Ser Val Leu Gln Val Lys Arg Leu Gln Leu Glu Leu
1               5                   10                  15

Ile Thr Pro Ala Lys Pro Thr Leu Gln Glu Ala Lys Phe Leu Ser Asp
            20                  25                  30

Ile Asp Asp Gln Glu Gly Leu Arg Phe Gln Val Pro Val Ile Met Cys
        35                  40                  45

Tyr Lys Asp Asn Pro Ser Leu Asn Lys Asn Cys Asn Pro Val Lys Val
    50                  55                  60

Ile Arg Glu Ala Leu Ser Arg Ala Leu Val Tyr Tyr Pro Leu Ala
65                  70                  75                  80

Gly Arg Leu Lys Glu Gly Pro Asn Arg Lys Leu Met Val Asp Cys Asn
                85                  90                  95

Gly Glu Gly Ile Leu Phe Val Glu Ala Ser Ala Asp Val Thr Leu Glu

```
            100                 105                 110
Gln Leu Gly Asp Lys Ile Leu Pro Pro Cys Pro Leu Leu Glu Glu Phe
        115                 120                 125

Leu Phe Asn Phe Pro Gly Ser Asp Gly Ile Ile Gly Cys Pro Leu Leu
130                 135                 140

Leu Val Gln Val Thr Cys Leu Thr Cys Gly Gly Phe Ile Leu Ala Leu
145                 150                 155                 160

Arg Val Asn His Thr Met Cys Asp Ala Pro Gly Leu Leu Leu Phe Leu
                165                 170                 175

Thr Ala Ile Ala Glu Met Ala Arg Gly Ala His Ala Pro Ser Ile Leu
            180                 185                 190

Pro Val Trp Glu Arg Glu Leu Leu Phe Ser Arg Asp Pro Pro Arg Ile
        195                 200                 205

Thr Cys Ala His His Glu Tyr Glu Asp Val Ile Asp His Ser Asp Gly
    210                 215                 220

Leu Tyr Ala Ser Ser Asn Gln Ser Asn Met Val Gln Arg Ser Phe Tyr
225                 230                 235                 240

Phe Gly Ala Lys Glu Met Arg Val Leu Arg Lys Gln Ile Pro Pro His
                245                 250                 255

Leu Ile Ser Thr Cys Ser Thr Phe Asp Leu Ile Thr Ala Cys Leu Trp
            260                 265                 270

Lys Cys Arg Thr Leu Ala Leu Asn Ile Asn Pro Lys Glu Ala Val Arg
        275                 280                 285

Val Ser Cys Ile Val Asn Ala Arg Gly Lys His Asn Asn Val Arg Leu
    290                 295                 300

Pro Leu Gly Tyr Tyr Gly Asn Ala Phe Ala Phe Pro Ala Ala Ile Ser
305                 310                 315                 320

Lys Ala Glu Pro Leu Cys Lys Asn Pro Leu Gly Tyr Ala Leu Glu Leu
                325                 330                 335

Val Lys Lys Ala Lys Ala Thr Met Asn Glu Glu Tyr Leu Arg Ser Val
            340                 345                 350

Ala Asp Leu Leu Val Leu Arg Gly Arg Pro Gln Tyr Ser Ser Thr Gly
        355                 360                 365

Ser Tyr Leu Ile Val Ser Asp Asn Thr Arg Ala Gly Phe Gly Asp Val
    370                 375                 380

Asn Phe Gly Trp Gly Gln Pro Val Phe Ala Gly Pro Ala Lys Ala Leu
385                 390                 395                 400

Asp Leu Ile Ser Phe Tyr Val Gln His Lys Asn Asn Thr Glu Asp Gly
                405                 410                 415

Ile Leu Val Pro Met Cys Leu Pro Ser Ser Ala Met Glu Arg Phe Gln
            420                 425                 430

Gln Glu Leu Glu Arg Ile Thr Gln Glu Pro Lys Glu Asp Ile Cys Asn
        435                 440                 445

Asn Leu Arg Ser Thr Arg Ile Met Ser Met Met
    450                 455
```

<210> SEQ ID NO 10
<211> LENGTH: 1380
<212> TYPE: DNA
<213> ORGANISM: Artificial Sequence
<220> FEATURE:
<223> OTHER INFORMATION: Yarrowia codon-optimized MdATF

<400> SEQUENCE: 10
atgatgccct tctctgttct ccaggttaag cgacttcagc ttgagcttat taccccctgcc    60

```
aagcccactc tccaggaggc taagtttctc tctgacatcg acgatcagga gggccttcga    120
tttcaggttc ctgtcattat gtgttacaag gataacccct ctcttaacaa gaactgtaac    180
cctgttaagg tgattcgaga ggctctttcc cgagctcttg tttactacta ccctctcgct    240
ggacgactta aggagggtcc taaccgaaag ctcatggtcg attgcaacgg tgagggtatt    300
ctgttcgttg aggcttctgc tgatgttacc cttgagcagc ttggtgataa gattcttccc    360
ccttgtcctc tccttgagga gttccttttc aactttcccg ttctgatgg tattattggt     420
tgtcctctcc ttctcgttca ggtcacttgc cttacctgtg gaggctttat tcttgcccct    480
cgagtcaacc acactatgtg tgatgctcct ggtctgctcc tgttcctgac cgccatcgct    540
gagatggccc gaggagctca cgctccttct attcttcccg tttgggagcg agagcttctc    600
ttttcccgag atcccctcg aattacttgt gctcaccacg agtacgagga cgttattgac      660
cactctgacg gtctttacgc ttcttccaac cagtctaaca tggttcagcg atctttctac    720
tttggtgcca aggagatgcg agttcttcga aagcagattc ctccccacct tatttctacc    780
tgctctacct ttgaccttat taccgcttgt ctttggaagt gtcgaaccct gctcttaac     840
attaaccccta aggaggctgt tcgagtttct tgcattgtta acgcccgagg aaagcacaac    900
aacgttcgac ttcccccttgg ttactacgga aacgcttttg cttttcccgc tgctatctct   960
aaggccgagc tctctgtaa gaaccccctt ggttacgctc ttgagcttgt caagaaggct   1020
aaggctacta tgaacgagga gtaccttcga tctgtggctg atctccttgt tcttcgagga   1080
cgacctcagt actcttctac cggatcttac cttattgttt ctgataacac ccgagctggt   1140
tttggtgatg ttaactttgg ttggggacag cccgtttttg ctggacccgc caaggcccctt   1200
gaccttattt ccttctacgt tcagcacaag aacaacactg aggatggtat tcttgttcct   1260
atgtgtctcc cttcctccgc tatggagcga tttcagcagg agcttgagcg aattactcag   1320
gagcctaagg aggatatttg taacaacctt cgatctactc gaatcatgtc tatgatgtaa   1380
```

<210> SEQ ID NO 11
<211> LENGTH: 465
<212> TYPE: PRT
<213> ORGANISM: Petunia x hybrida

<400> SEQUENCE: 11

Met Cys Pro Lys Leu Ala Arg Ile Asn Ser Tyr Met Gly Asn Thr Asp
1               5                   10                  15

Phe His Val Thr Val Lys Lys Lys Glu Val Ala Ala Val Leu Pro
            20                  25                  30

Met His His Glu His Trp Leu Pro Met Ser Asn Leu Asp Leu Leu Leu
        35                  40                  45

Pro Pro Leu Asp Phe Gly Val Phe Phe Cys Tyr Lys Arg Ser Lys Ile
    50                  55                  60

Asn Asn Asp Thr Lys Asp Asp Glu Thr Ile Lys Lys Ala Leu Ala
65                  70                  75                  80

Glu Thr Leu Val Ser Phe Tyr Ala Leu Ala Gly Glu Val Val Phe Asn
                85                  90                  95

Ser Leu Gly Glu Pro Glu Leu Leu Cys Asn Asn Arg Gly Val Asp Phe
            100                 105                 110

Phe His Ala Tyr Ala Asp Ile Glu Leu Asn Asn Leu Asp Leu Tyr His
        115                 120                 125

Pro Asp Val Ser Val His Glu Lys Leu Ile Pro Ile Lys Lys His Gly
    130                 135                 140

Val Leu Ser Val Gln Val Thr Gly Leu Lys Cys Gly Gly Ile Val Val
145                 150                 155                 160

Gly Cys Thr Phe Asp His Arg Val Ala Asp Ala Tyr Ser Ala Asn Met
            165                 170                 175

Phe Leu Val Ala Trp Ala Ala Ile Ala Arg Lys Asp Asn Asn Ile Asn
            180                 185                 190

Thr Val Ile Pro Ser Phe Arg Arg Ser Leu Leu Asn Pro Arg Arg Pro
            195                 200                 205

Pro Gln Phe Asp Asp Ser Phe Ile Asp Ser Thr Tyr Val Phe Leu Ser
            210                 215                 220

Ser Pro Pro Lys Gln Pro Asn Asp Val Leu Thr Ser Arg Val Tyr Tyr
225                 230                 235                 240

Ile Asn Ser Gln Glu Ile Asn Leu Leu Gln Ser Gln Ala Thr Arg Asn
            245                 250                 255

Gly Ser Lys Arg Ser Lys Leu Glu Cys Phe Ser Ala Phe Leu Trp Lys
            260                 265                 270

Thr Ile Ala Glu Gly Gly Ile Asp Asp Ser Lys Arg Cys Lys Leu Gly
            275                 280                 285

Ile Val Val Asp Gly Arg Gln Arg Leu Arg His Asp Ser Ser Thr Thr
            290                 295                 300

Met Lys Asn Tyr Phe Gly Asn Val Leu Ser Val Pro Tyr Thr Glu Ala
305                 310                 315                 320

Ser Val Gly Gln Leu Lys Gln Thr Pro Leu Gly Lys Val Ala Asp Leu
            325                 330                 335

Val His Thr Cys Leu Asp Asn Val Ala Asn Glu His His Phe Pro Ser
            340                 345                 350

Leu Ile Asp Trp Val Glu Leu His Arg Pro Arg Gln Ala Ile Val Lys
            355                 360                 365

Val Tyr Cys Lys Asp Glu Cys Asn Asp Glu Ala Ala Ile Val Val Ser
            370                 375                 380

Ser Gly Leu Arg Phe Pro Leu Ser Gln Val Asn Phe Gly Trp Gly Cys
385                 390                 395                 400

Pro Asp Phe Gly Ser Tyr Ile Phe Pro Trp Gly Gly Gln Thr Gly Tyr
            405                 410                 415

Val Met Pro Met Pro Ser Pro Asn Lys Asn Gly Asp Trp Ile Val Tyr
            420                 425                 430

Met His Leu Gln Lys Lys His Leu Asp Leu Val Glu Thr Arg Ala Pro
            435                 440                 445

His Ile Phe His Pro Leu Thr Ala Cys Tyr Leu Asp Leu Thr Ala Thr
            450                 455                 460

Tyr
465

<210> SEQ ID NO 12
<211> LENGTH: 1398
<212> TYPE: DNA
<213> ORGANISM: Artificial Sequence
<220> FEATURE:
<223> OTHER INFORMATION: Yarrowia codon-optimized PhATF

<400> SEQUENCE: 12
atgtgcccta agctcgctcg aattaactct tacatgggaa acactgactt tcacgttacc      60
gtcaagaaga aggaggttgt ggctgctgtt ctccctatgc accacgagca ctggcttccc     120
atgtccaacc ttgaccttct ccttcccccct ctcgactttg gtgttttctt ctgctacaag    180

```
cgatctaaga ttaacaacga taccaaggat gacgatgaga ctattaagaa ggctcttgct    240
gagactctcg tttcttttta cgctcttgct ggagaggtgg ttttcaactc tctcggagag    300
cccgagcttc tctgtaacaa ccgaggagtt gatttctttc acgcttacgc tgatattgag    360
ctcaacaacc ttgaccttta ccaccccgat gtctctgttc acgagaagct gattcctatc    420
aagaagcacg gcgttctctc tgttcaggtc actggcctta agtgtggagg tatcgttgtt    480
ggatgcactt tcgatcaccg agttgctgat gcttactctg ctaacatgtt ccttgttgct    540
tgggctgcta ttgctcgaaa ggataacaac attaacactg ttatcccttc tttccgacga    600
tccctcctta accctcgacg acctccccag tttgacgatt cctttatcga ctccacctac    660
gttttccttt cttctccccc taagcagcct aacgatgtcc tcacttcccg agtgtactac    720
attaactctc aggagattaa cctccttcag tctcaggcta ctcgaaacgg atctaagcga    780
tctaagctgg agtgtttctc cgcctttctc tggaagacta ttgctgaggg aggtattgac    840
gattctaagc gatgtaagct cggaattgtt gtcgatggcc gacagcgact gcgacacgac    900
tcttctacca ccatgaagaa ctactttggc aacgttcttt ctgttcctta cactgaggct    960
tctgttggac agctcaagca gactccccct tggtaaggttg ctgaccttgt tcacacttgc   1020
ctcgataacg ttgctaacga gcaccacttt ccctctctca ttgactgggt tgagcttcac   1080
cgacctcgac aggctattgt taaggtttac tgtaaggatg agtgtaacga tgaggctgcc   1140
atcgttgtct cctctggact ccgatttccc ctttctcagg ttaactttgg ctggggctgt   1200
cctgactttg gctcttacat tttcccttgg ggcggtcaga ctggttacgt gatgcctatg   1260
ccttctccca acaagaacgg tgattggatt gtttacatgc accttcagaa gaagcacctt   1320
gaccttgtcg agactcgagc ccctcacatc ttccaccccc ttaccgcttg ttacctcgat   1380
ctcactgcta cttactaa                                                 1398
```

<210> SEQ ID NO 13
<211> LENGTH: 559
<212> TYPE: PRT
<213> ORGANISM: Lachancea mirantina

<400> SEQUENCE: 13

```
Met Gly Asp Leu Asp Ala Arg Gly Thr Ser Ala His Pro Glu Leu Ser
1               5                   10                  15

Glu Arg Pro Ser Ile Met Pro Ser Met Ser Asp Ile Gln Asp Pro Ser
            20                  25                  30

Gly Asp Asp Lys Ala Thr Pro Arg Gly Ser Ala Ala Gly Leu Pro Gln
        35                  40                  45

Leu Glu Leu Ala Gly His Ala Arg Arg Leu Gly His Leu Glu Asn Phe
    50                  55                  60

Phe Ala Val Gln His Arg Gln Gln Ile Tyr Ser Ser Phe Ala Val Phe
65                  70                  75                  80

Cys Glu Phe Asp Thr Ala Cys Ser Leu Ala Gln Leu Ala Ser Ala Val
                85                  90                  95

Arg Asn Val Cys Leu Ser Asn Pro Leu Leu Leu His Thr Val Glu Pro
            100                 105                 110

Lys His Pro Asp Ile Ala Gly Phe Tyr His Ser Asp Glu Tyr Leu Ser
        115                 120                 125

Arg Pro Trp Pro Gln His Asp Tyr Met Arg Val Leu Arg Glu Val His
    130                 135                 140

Val Ala Asp Val Val Met Asn Gly Gln Lys Glu His Ala His Val Val
```

```
                145                 150                 155                 160
Arg Asp Ala Val Asp Val Phe Gln Ala His Gly Asn Gln Val Thr Ser
                    165                 170                 175
Glu Leu Leu Glu Leu Met Thr Gln Ile Glu Ile Pro His Ala Ser Gln
                    180                 185                 190
Thr Arg Pro Ser Trp Arg Leu Leu Cys Phe Pro His Gly Glu Ala Asn
                    195                 200                 205
Arg Trp Arg Thr Phe Ala Phe Val Ser Asn His Cys Ser Ser Asp Gly
                    210                 215                 220
Leu Ser Gly Leu Asn Phe Phe Arg Asp Leu Gln Lys Glu Leu Ala His
225                 230                 235                 240
Gly Pro Thr Ser Gly Ala Pro Gly Ala Pro Gly Ala Ser Gly Val Ile
                    245                 250                 255
Phe Asp Tyr Ala Gln Asp Ala Ala Thr Leu Pro Lys Leu Pro Pro Pro
                    260                 265                 270
Ile Asp Gln Lys Leu Asp Tyr Arg Pro Ser Lys Lys Ala Leu Leu Gly
                    275                 280                 285
Leu Leu Ala Gly Lys Phe Val Arg Glu Lys Leu Gly Tyr Val Ser Ala
                    290                 295                 300
Ala Pro Pro Thr Thr Pro Thr Ser Asp Leu Ala His Pro Glu Gly His
305                 310                 315                 320
Gln Tyr Tyr Cys Tyr Leu Val Asn Val Pro Thr Ser Ser Val Ala His
                    325                 330                 335
Ile Lys Thr Gln Val Arg Glu Asn Val Pro His Lys Cys Thr Leu Thr
                    340                 345                 350
Pro Phe Leu Gln Ala Cys Trp Leu Val Ser Leu Phe Lys Tyr Gly Arg
                    355                 360                 365
Val Phe Ser Gly Ser Trp Leu Glu Arg Tyr Thr Asp Val Leu Val Ala
                    370                 375                 380
Met Asn Thr Arg Gln Leu Leu Pro Glu Asp Leu Glu Leu Gln Arg Gln
385                 390                 395                 400
Tyr Arg Tyr Gly Ser Asn Val Gly Gly Val Arg Tyr Asn Tyr Pro Ile
                    405                 410                 415
Ala Pro Leu Asp Val Arg Asp Asn Asp Gln Lys Phe Trp Ser Leu Val
                    420                 425                 430
Glu Ser Tyr Arg Leu Ala Leu Ser Asp Ala Arg Asp Lys Asn Asp Tyr
                    435                 440                 445
Leu Tyr Ala Leu Gly Ala Leu Met Leu Pro Glu Ile Tyr Glu Lys Lys
                    450                 455                 460
Asn Val Asp Ala Val Val Asn Asp Thr Ile Leu Asn Gln Arg Arg Ser
465                 470                 475                 480
Gly Thr Leu Ile Ser Asn Val Gly Tyr Val Arg Asp Glu Gln Pro Thr
                    485                 490                 495
Ala Phe Ala Ile Lys Asn His Val Phe Ser Gln Gly Val Gly Ala Asn
                    500                 505                 510
Arg Asn Ala Phe Val Leu Asn Ile Cys Ala Thr Asp Gln Gly Gly Leu
                    515                 520                 525
Asn Ile Ala Ile Ser Ile Ala Lys Gly Thr Leu Ala Ser Arg Gln Glu
                    530                 535                 540
Gly Gln Glu Leu Cys Asp Ile Phe Lys Ser Thr Leu Leu Arg Phe
545                 550                 555

<210> SEQ ID NO 14
```

```
<211> LENGTH: 1680
<212> TYPE: DNA
<213> ORGANISM: Lachancea mirantina

<400> SEQUENCE: 14
atgggtgatc tcgacgcgag gggaacatca gcgcacccgg agctctcgga gaggccaagc      60
atcatgccct cgatgtcgga tatccaggac ccaagcggcg acgacaaggc cacgccccgc     120
ggctccgccg cggggctgcc gcagctcgag ctcgccggcc acgcccggcg cctgggccat     180
ttggagaatt tcttcgccgt ccagcaccgg cagcagatct attccagttt cgccgtgttc     240
tgcgagttcg acaccgcgtg ctcgctcgcg cagctcgcgt ccgctgtgcg aaacgtgtgt     300
ctttcgaacc cgctgctgct gcacaccgtc gagcccaagc acccggacat cgccggcttc     360
taccactccg acgaatatct gtcccgaccc tggcccagc acgactacat gcgcgttttg      420
cgcgaggtcc acgtcgccga cgtggtgatg aacggccaga aagagcacgc gcatgtcgtg     480
cgcgacgccg tcgacgtttt ccaagcgcat ggaaaccagg tcaccagcga gctgctcgag     540
ctcatgaccc agattgagat cccgcacgct tcccaaacga cccagctg gaggttgctg       600 tgtttcccac acggcgaggc caaccggtgg cgcacgtttg cgtttgtatc caatcattgt     660
tccagcgacg gtctctcggg tctgaacttc tttcgggacc tgcaaaagga gctcgcgcac     720
ggccccacct cggggggccc cggggccccg ggggcctccg gcgtcatctt cgactacgcc     780
caggacgccg caacactgcc caaactgccc ccacccattg accaaaaact cgattaccgt     840
ccgtccaaga aggcccttttt gggactttttg ccggcaagt tcgtgcgtga aaaactcggc     900
tacgtatcgg ccgccccgcc aacgacccccg acctccgatt tggcgcaccc agaaggtcac     960
caatactact gctaccttgt aaacgtaccg acatctagtg tggcccacat caaaacgcaa    1020
gtgcgcgaaa atgtcccgca caaatgcacg ctgacgccat tcttacaggc atgctggctc    1080
gtgtcactgt tcaagtatgg tcgcgttttt tccggctcct ggctcgaacg atacacggac    1140
gttctcgtcg ctatgaacac ccggcaactg ttgcccgaag attggaatt gcaacgccag     1200 taccgttacg gtagtaacgt gggaggggta cgttacaatt atccaatcgc accgctcgac    1260
gtccgcgaca cgaccagaa attctggtcc ctggtggaga gttaccgact ggcccttagc     1320
gacgcacgcg acaaaaatga ttacttgtac gcattgggtg ctctaatgct tccagagatc    1380
tacgaaaaaa aaaacgtcga tgctgtggtc aatgacacaa ttctgaacca gcgtcgttcc    1440
ggaacgttga tcagtaacgt cggctacgtg cgcgatgaac agcccactgc gtttgcaatt    1500
aagaatcatg tcttttcaca aggcgttggc gccaacagaa acgcatttgt gcttaacata    1560
tgtgccacgg accaaggcgg cctaaatatc gccatcagta tcgccaaggg aaccttggcg    1620
tctcgtcaag aaggccaaga actttgcgac atctttaaat caacgttact gcgattctaa    1680

<210> SEQ ID NO 15
<211> LENGTH: 1680
<212> TYPE: DNA
<213> ORGANISM: Artificial Sequence
<220> FEATURE:
<223> OTHER INFORMATION: Yarrowia codon optimized LmATF1

<400> SEQUENCE: 15
atgggtgatc tcgatgcccg aggaaccctc tgctcacccc g agctctctga gcgaccttct    60
attatgcctt ctatgtctga tattcaggac ccttctggtg atgacaaggc tactccccga     120
ggatctgctg ctgggctgcc ccagcttgag cttgctggac acgcccgacg acttggccac     180
cttgagaact tctttgctgt ccagcaccga cagcagattt actcttcttt tgctgtttttt    240
```

```
tgtgagtttg acactgcttg ttctctcgct cagcttgctt ctgctgtgcg aaacgtttgt      300
ctttctaacc cccttctcct tcacactgtt gagcctaagc accctgacat cgctggattc      360
taccactctg acgagtacct ttcccgacct tggcctcagc acgattacat gcgagttctt      420
cgagaggttc acgtcgctga cgttgttatg aacggacaga aggagcacgc tcacgttgtt      480
cgagatgctg ttgacgtttt tcaggctcac ggaaaccagg ttacttctga gctccttgag      540
cttatgactc agattgagat tcctcacgct tctcagactc gaccctcttg gcgacttctc      600
tgttttcccc acggagaggc taaccgatgg cgaacctttg cttttgtttc taaccactgt      660
tcttctgatg gtctttctgg tcttaacttc tttcgagatc tccagaagga gcttgctcac      720
ggccccacct ctggtgctcc tggtgccccc ggagcttccg gagttatttt cgattacgct      780
caggacgctg ctaccctgcc caagctgccc cctcccattg atcagaagct cgattaccga      840
ccttctaaga aggctcttct cggccttctc gctggcaagt cgttcgaga  aagctcggt       900
tacgtttctg ctgctcctcc cactacccct acctctgacc ttgctcaccc tgagggtcac      960
cagtactact gttaccttgt taacgttccc acttcttctg ttgcccacat taagactcag     1020
gtgcgagaga acgttcctca caagtgtact ctcactccct ttctccaggc ttgttggctt     1080
gtttctctgt tcaagtacgg tcgagttttt tctggttctt ggcttgagcg atacaccgat     1140
gttcttgttg ctatgaacac tcgacagctt ctccccgagg accttgagct tcagcgacag     1200
taccgatacg gttctaacgt tggaggtgtt cgatacaact accctattgc tccccttgac     1260
gttcgagata cgatcagaa  gttctggtcc cttgttgagt cttaccgact tgcccttct      1320
gatgcccgag ataagaacga ttacctttac gctcttggtg ctcttatgct ccctgagatt     1380
tacgagaaga agaacgttga tgctgttgtt aacgatacca ttcttaacca gcgacgatct     1440
ggaaccctta tttctaacgt tggttacgtt cgagatgagc agcccactgc ttttgctatt     1500
aagaaccacg ttttttctca gggagttgga gctaaccgaa acgcttttgt tcttaacatt     1560
tgtgctaccg atcagggtgg tcttaacatc gctatttcta ttgctaaggg aacccttgct     1620
tctcgacagg agggacagga gctttgtgat atttttaagt ctactctcct tcgatttta      1680
```

<210> SEQ ID NO 16
<211> LENGTH: 536
<212> TYPE: PRT
<213> ORGANISM: Lachancea fermentata

<400> SEQUENCE: 16

Met Ile Ile Ile Leu Thr Lys Pro Lys Phe Pro Ser Ser Asn Ser Arg
1               5                   10                  15

Ser Leu Glu Ile Lys Leu Asn Asn Met Pro Pro Gly Thr Leu Leu Arg
            20                  25                  30

Glu Met Ile Glu Asn Gly His Ala Arg Pro Met Gly Ser Ile Glu Asn
        35                  40                  45

Ile Tyr Gly Ile Phe Asn Arg Gln Lys Leu Tyr Arg Asn Phe Ser Met
    50                  55                  60

Phe Ala Glu Ile Asn Asp Phe Cys Asn Glu Arg Gln Leu Arg Ala Ala
65                  70                  75                  80

Leu Arg Asn Leu Cys Leu Lys Asn Pro Ile Leu His Thr Ile Val
                85                  90                  95

Pro Glu Ile Trp Pro Phe Asn Glu Lys Tyr Tyr Leu Ser Asp Glu Tyr
            100                 105                 110

Tyr Cys Met Pro Arg Ser Gln His Glu Phe Ile Ala Ile Leu Pro Glu

-continued

```
            115                 120                 125
Leu Asp Leu Ser Asp Ile Leu Ala Asn Lys Gln Thr Gln Tyr Gln Gln
        130                 135                 140

Val Leu Glu Lys Ala Phe Arg Glu Phe Glu Ser Ser Asn Phe Cys Tyr
145                 150                 155                 160

Thr Ser Glu Val Tyr Lys Leu Ile Ala Thr Ile Ser Ile Pro Tyr Val
                165                 170                 175

Gly Pro Ser Trp Arg Leu Ile Cys Leu Pro Glu Lys Arg Gly Thr Glu
                180                 185                 190

Trp Arg Lys Phe Ile Phe Ile Ser Asn His Cys Leu Cys Asp Gly Arg
                195                 200                 205

Ser Ala Ala Asn Phe Phe His Asp Leu Lys Glu Glu Leu Asn Cys Asn
        210                 215                 220

Ile Asp Asn Arg Leu Thr Val Thr Thr Ile Phe Ser Tyr Glu Arg Asp
225                 230                 235                 240

His Tyr Leu Leu Pro Lys Leu Pro Glu Pro Leu Glu Lys Arg Ile Asp
                245                 250                 255

Phe Arg Pro Pro Trp Ser Tyr Phe Pro Lys Tyr Leu Val Trp Glu Pro
                260                 265                 270

Ile Val Asn His Phe Lys Phe Ser Ser Asn Cys Ala Thr Ser Arg Leu
                275                 280                 285

Asp Glu Ser Phe Asp Gly Lys Thr Leu Leu Thr Glu Ile Ile Asn Ile
        290                 295                 300

Asp Val Gln Val Leu Glu Lys Val Arg Gln Leu Ile Lys Ala Asn Val
305                 310                 315                 320

His Glu Gly Gly Thr Ile Thr Pro Phe Leu Glu Ile Cys Trp Leu Ile
                325                 330                 335

Ser Leu His Lys Trp Gly Ala Phe Ser Gly Lys Ser Trp Thr Lys Cys
                340                 345                 350

Leu Thr Asp Val Phe Val Pro Val Asp Val Arg Asn Leu Leu Pro Asp
        355                 360                 365

Asp Asp Asp Ile Arg Lys Ser Tyr Arg Tyr Gly Cys Asn Val Ala Ala
        370                 375                 380

Ile Glu Leu Asn Pro Trp Ile Ser Gln Leu Asp Val Glu Lys Asn Ser
385                 390                 395                 400

Asp Glu Phe Trp Ala Leu Val Ser Gln Asn Gln Asn Lys Ile Thr Ser
                405                 410                 415

Leu Leu Gln Lys Lys Glu Gln Leu Asn Leu Ile Gly Phe Asn Thr Leu
                420                 425                 430

Asp Ile Val Glu Lys Asn Phe Asn Leu Asp Arg Glu Leu Cys Val His
        435                 440                 445

Thr Leu Asn Lys Pro Arg Gln Gly Thr Leu Leu Ser Asn Leu Gly Ile
        450                 455                 460

Phe Pro Gln Asn Ser Gln Glu Arg Asp Arg Tyr Ser Leu Glu Asn Leu
465                 470                 475                 480

Ile Phe Gly Gln Phe Gln Gly Ser Phe Arg Glu Ser Phe Ser Met Cys
                485                 490                 495

Val Cys Ser Thr Asp Arg Lys Gly Met Asn Ile Val Leu Thr Thr Thr
                500                 505                 510

Ser Asp Leu Ile Pro Asn Ser Lys Ser Trp Glu Asp Leu Cys Ser Thr
        515                 520                 525

Phe Lys Ser Ile Ile Ser Asp Thr
        530                 535
```

<210> SEQ ID NO 17
<211> LENGTH: 1611
<212> TYPE: DNA
<213> ORGANISM: Artificial Sequence
<220> FEATURE:
<223> OTHER INFORMATION: Yarrowia codon optimized LfATF1

<400> SEQUENCE: 17

```
atgatcatta ttctcactaa gcctaagttc ccttcctcca actctcgatc cctggagatc      60
aagctgaaca acatgccccc tggtactctc ctgcgagaga tgatcgagaa cggacacgcc     120
cgacctatgg gctccattga gaacatttac ggaattttta accgacagaa gctctaccga     180
aactttttcta tgtttgccga gatcaacgac ttttgtaacg agcgacagct tcgagccgcc     240
ctgcgaaacc tgtgtcttaa gaaccctatt ctccttcaca ccattgtccc cgagatttgg     300
cctttcaacg agaagtacta cctgtctgac gagtactact gtatgcctcg atctcagcac     360
gagtttatcg ctattctgcc cgagctcgac ctgtccgata ttctggccaa caagcagacc     420
cagtaccagc aggttctgga aaggctttc cgagagttcg agtcctccaa cttttgttac     480
acctctgagg tgtacaagct gattgctact atttctatcc cttacgtggg ccctctcttgg     540
cgacttattt gcctccctga agcgagga accgagtggc gaaagttcat cttcatttcc     600
aaccactgtc tctgtgatgg tcgatccgcc gccaacttttt tccacgacct gaaggaggag     660
ctgaactgta acattgacaa ccgacttacc gtcactacca tttttctctta cgagcgagat     720
cactaccttc tccccaagct gcccgagccc ctggagaagc gaattgatttt ccgaccccct     780
tggtcttact ttcccaagta ccttgtctgg agcccatcg tgaaccactt caagttctcc     840
tctaactgcg ctactcccg actcgatgag tcttctcgacg taagactct ccttaccgag     900
attattaaca ttgacgtgca ggtccttgag aaggttcgac agctcatcaa ggccaacgtg     960
cacgagggtg gtactatcac ccctttcctt gagatttgtt ggctcatttc ccttcacaag    1020
tggggagctt tctctggtaa gtcctggact aagtgcctca ccgatgtttt tgttcccgtc    1080
gatgtccgaa accttctccc tgacgacgat gacatccgaa agtcttaccg atacggctgt    1140
aacgttgctg ctatcgagct taaccccttgg atctctcagc tcgatgtcga agaactcc    1200
gatgagtttt gggcccttgt ttcccagaac cagaacaaga tcacctccct cctccagaag    1260
aaggagcagc tcaacctcat tggctttaac ccctcgata ttgtcgagaa aactttaac    1320
ctcgaccgag agctctgcgt ccacactctc aacaagcccc gacagggtac tctcctgtcc    1380
aacctgggta ttttccctca gaactcccag gagcgagatc gatactccct ggagaacctg    1440
atttttggtc agtttcaggg ttccttccga gagtctttct ctatgtgtgt ctgttccacc    1500
gatcgaaagg gaatgaacat tgttctcacc actacctctg atctcatccc caactccaag    1560
tcctgggagg accttttgctc taccttcaag tctattatct ccgacactta g            1611
```

<210> SEQ ID NO 18
<211> LENGTH: 515
<212> TYPE: PRT
<213> ORGANISM: Lachancea fermentata

<400> SEQUENCE: 18

Met Tyr Glu Ser Leu Gln Thr Leu Ile Glu Arg Gly His Ala Arg Arg
1               5                   10                  15

Leu Gly His Val Glu Asn Tyr Phe Val Leu Ala Gln Arg Gln Asp Leu
            20                  25                  30

```
Tyr Arg Val Phe Ala Tyr Tyr Gly Glu Phe Gly Glu Pro Cys Ser Leu
            35                  40                  45
Arg Gln Leu Thr Gln Ala Leu Arg Ser Met Cys Leu Gln Gln Pro Val
 50                  55                  60
Leu Leu Cys Gln Val Lys Pro Gln Glu Arg Pro Asp Leu Glu Leu Tyr
 65                  70                  75                  80
Tyr Arg Ser Glu Glu Tyr Leu Ser Thr Pro Gly Gln Asp Arg Asp Tyr
                 85                  90                  95
Ile Ala Leu Ala Asn Lys Val Arg Ile Ser Asp Val Leu Ile Asn Asn
                100                 105                 110
Gln Thr Glu Tyr Ala Glu Val Met His Lys Val Met Glu Glu Tyr Glu
                115                 120                 125
Ala Asn Gly His Asn Phe Thr Ser Lys Ile Phe Glu Ile Leu Ala Pro
130                 135                 140
Ile Arg Ile Ser His Thr Asp Pro Asn Lys Leu Asn Trp Arg Leu Leu
145                 150                 155                 160
Ala Leu Pro Gly Glu Ile Pro Gly Glu Trp Asn Lys Phe Val Phe Leu
                165                 170                 175
Ser Asn His Ile Leu Lys Asp Gly Ser Ser Gly Ala His Phe Phe Ile
                180                 185                 190
Asp Leu Lys Asp Ser Leu Asn Ser Leu Pro Ser Asp Leu Gln Asp Thr
                195                 200                 205
Asp Arg Ile Phe Asp Tyr Lys Ser Asp Tyr Lys Phe Val Lys Glu Ile
                210                 215                 220
Pro Val Pro Ile Asp Glu Val Leu Asp Tyr Lys Pro Asn Leu Lys Gln
225                 230                 235                 240
Ile Ala Asn Val Phe Ser Thr Gln Leu Val Arg Glu Lys Leu Gly Tyr
                245                 250                 255
Leu Ser Pro Ala Pro Thr Ile Thr Arg Tyr Thr Asp Ala Glu Asn Asn
                260                 265                 270
Thr Asn Glu Tyr His Thr Cys Phe Ile Asn Phe Thr Pro Glu Glu Val
                275                 280                 285
Asp Ser Ile Lys Lys Lys Ile Lys Asp Arg Ala Gly Pro Ser Cys Thr
290                 295                 300
Met Thr Pro Phe Leu Gln Ala Cys Trp Leu Val Ser Leu Tyr Lys Ser
305                 310                 315                 320
Gly Lys Val Phe Thr Lys Ser Phe Lys Glu Trp Phe Val Asp Met Met
                325                 330                 335
Ile Pro Met Tyr Thr Pro Gln Met Leu Ser Asp Gly Glu Gln Thr Arg
                340                 345                 350
Ala Asp Tyr Arg Tyr Gly Cys Asn Val Gly Gly Thr Arg Tyr Asn Tyr
                355                 360                 365
Leu Ile Ser Ser Leu Asn Val Gly Asn Asn Ser Lys Lys Phe Trp Lys
                370                 375                 380
Leu Val Ser Tyr Tyr Asn Asp Val Phe Arg Asp Ser Lys Ala Ser Asn
385                 390                 395                 400
Ser Tyr Leu Tyr Leu Ile Gly Met Ile Met Leu Asp Pro Ala Trp Lys
                405                 410                 415
Glu Lys Asn Leu Asp Ala Thr Val Leu Gln Asn Leu Leu Gly Arg His
                420                 425                 430
Arg Gln Gly Thr Val Leu Ser Asn Val Gly Phe Phe Ser Val Asn Gly
                435                 440                 445
Glu Pro Gln Asp Ala Phe His Leu Lys Asn Leu Leu Phe Thr Gln Thr
```

|     |     |     |     |     | 450 |     |     |     |     | 455 |     |     |     |     | 460 |     |
| --- | --- | --- | --- | --- | --- | --- | --- | --- | --- | --- | --- | --- | --- | --- | --- | --- |
| Val | Gly | Ser | Tyr | Thr | Phe | Ala | Phe | Asn | Leu | Asn | Val | Cys | Ser | Thr | Asp |     |
| 465 |     |     |     | 470 |     |     |     | 475 |     |     |     |     | 480 |     |     |     |

Val Ala Gly Met Asn Val Gly Ala Ser Val Ser Lys Gly Thr Leu Pro
                485                 490                 495

Thr Arg Asn Asp Trp Glu Glu Leu Cys Glu Ile Phe Lys Thr Thr Val
            500                 505                 510

Leu Gln Met
    515

<210> SEQ ID NO 19
<211> LENGTH: 1548
<212> TYPE: DNA
<213> ORGANISM: Artificial Sequence
<220> FEATURE:
<223> OTHER INFORMATION: Yarrowia codon optimized LffATF1

<400> SEQUENCE: 19

```
atgtacgagt cccttcagac tctcatcgag cgaggacacg ctcgacgact cggccacgtg     60
gagaactact ttgttctcgc tcagcgacag gatctctacc gagttttcgc ttactacgga    120
gagttcggag agccttgctc ccttcgacac ctcactcagg ccctccgatc tatgtgtctt    180
cagcagcctg ttctgctctg ccaggtcaag ccccaggagc gacctgacct cgagctttac    240
taccgatctg aggagtacct gtctactccc ggacaggatc gagattacat cgctcttgct    300
aacaaggtgc gaatctccga tgtccttatc aacaaccaga ctgagtacgc tgaggtcatg    360
cacaaggtta tggaggagta cgaggctaac ggccacaact ttacctctaa gattttt gag    420
attctcgccc ctattcgaat ctctcacacc gatcccaaca agctgaactg gcgactcctt    480
gctcttcccg gagagatccc tggtgagtgg aacaagtttg tcttcctttc aaccacatt     540
cttaaggatg gctcctctgg cgctcacttt ttcattgatc tcaaggattc tctgaactct    600
ctcccttctg acctccagga taccgaccga attttcgatt acagtccga ctacaagttt     660
gttaaggaga tccccgtccc tatcgatgag gttcttgact acaagcctaa ccttaagcag    720
attgctaacg tctttttctac tcagcttgtt cgagagaagc tgggttacct ctctcctgct    780
cctaccatta ctcgatacac cgatgctgag aacaacacta cgagtacca cacttgcttt    840
attaactta cccctgagga ggttgattct atcaagaaga agattaagga tcgagccggc    900
ccttcttgca ctatgacccc ttt ccttcag gcttgctggc tggtttccct ttacaagtcc    960
ggcaaggttt tcactaagtc tttcaaggag tggttcgtgg acatgatgat ccctatgtac   1020
acccccaga  tgctctctga cggcgagcag acccgagctg actaccgata cggctgtaac   1080
gttggaggta ctcgatacaa ctacctcatc tcctctctta cgttggaaa caactccaag   1140
aagtttt gga agctggttc ttactacaac gatgtcttcc gagactctaa ggcctccaac   1200
tcttaccttt accttatcgg aatgatcatg cttgaccctg cttggaagga gaagaacctg   1260
gacgccactg tccttcagaa cctccttggt cgacaccgac agggcactgt tctgtctaac   1320
gttggattct tttctgtgaa cggagagccc caggatgctt tcaccttaa gaaccttctc   1380
tttacccaga ctgttggttc ttacacctttgctttcaacc tcaacgtctg ctctactgac   1440
gtggccggaa tgaacgttgg cgcttctgtg tctaagggca ccctgcccac tcgaaacgac   1500
tgggaggagc tttgcgagat cttcaagact accgttctcc agatgtaa               1548
```

PRODUCTION OF RETINYL ESTERS

This application is the U.S. national phase of International Application No. PCT/EP2018/076034, filed 25 Sep. 2018 which designated the U.S. and claims the benefit of U.S. Application No. 62/562,672 filed 25 Sep. 2017, claims priority to EP Patent Application No. 18168564.5 filed 20 Apr. 2018, the entire contents of each of which are hereby incorporated by reference.

The present invention is related to production of retinyl esters, such as in particular retinyl acetate, an important building block for production of vitamin A. The retinyl esters might be generated via enzymatic conversion of retinol which process includes the use of enzymes with acetyl-transferase (ATF) activity, thus acetylating retinol into retinol/retinyl acetate. Said process is particularly useful for biotechnological production of vitamin A.

Retinyl esters, particularly retinyl acetate, are important intermediates or precursors for production of retinoids, particularly such as vitamin A. Retinoids, including vitamin A, are one of very important and indispensable nutrient factors for human beings which have to be supplied via diet. Retinoids promote well-being of humans, inter alia in respect of vision, the immune system and growth.

Current chemical production methods for retinoids, particularly vitamin A and precursors thereof, have some undesirable characteristics such as e.g. high-energy consumption, complicated purification steps and/or undesirable by-products. Therefore, over the past decades, other approaches to manufacture retinoids, particularly vitamin A and precursors thereof, have been investigated, including microbial conversion steps, which would be more economical as well as ecological.

In general, the biological systems that produce retinoids are industrially intractable and/or produce the compounds at such low levels that its isolation on industrial scale is not practicable of economic interest. There are several reasons for this, including instability of the retinoids in such biological systems or the relatively high production of by-products.

Acetylation of carotenoids, such as e.g. astaxanthin, by action of Atf1 from *Saccharomyces bayanus* has been previously reported (WO2014096992). However, these enzymes usually have very narrow substrate specificity, in as much as the acetylated hydroxy group in astaxanthin is located on the beta-ionone ring structure, whereas the acetylated hydroxy group on retinol is on the aliphatic end of the molecule and not on the beta-ionone ring. Therefore, these acetylated hydroxy functions are each in a very different local structural context, and thus different ATF enzymes with slight structural changes in their active site, can have very different affinities for these hydroxy groups on retinoids versus carotenoids. Thus, from the activity of SbATF1 on carotenoids as disclosed previously, the skilled person cannot predict how the action would be on retinoids.

Thus, it is an ongoing task to look for alternative (biotech) routes including the use of enzymes having improved product-specificity and/or productivity towards conversion of beta-carotene into retinoid building blocks for production of vitamin A. Particularly, it is desirable to optimize the productivity of enzymes involved in conversion of retinol towards retinyl esters, such as e.g. retinyl acetate.

Surprisingly, we now could identify specific acetyl transferases (ATFs) which are capable of converting retinol, preferably trans-retinol, into retinyl ester, particularly retinyl acetate, with a total conversion of at least about 10% towards generation of retinyl esters, e.g. retinyl acetate.

In particular, the present invention is directed to acetylating enzymes [EC 2.3.1.84], particularly Atf1, which are expressed in a suitable host cell, such as a carotenoid-producing host cell, particularly fungal host cell, with the activity of acetylating retinol into retinyl esters, particularly retinyl acetate, with a total conversion towards production of retinyl acetate of at least about 10%, preferably 12, 15, 20, 30, 40, 50, 80, 90 or even 100% based on the total amount of retinoids within the retinoid mix produced by said host cell, i.e. an amount of retinyl esters, particularly retinyl acetate, of at least 10% compared to the amount of retinol present in said retinoid mix produced by the host cell. The Atf1 enzymes as defined herein are particularly useful for acetylation of trans-retinol or a retinol-mix comprising cis- and trans-retinol with a percentage of at least 65% or trans-retinol, resulting in the formation of trans-retinyl esters.

The terms "acetyl transferase", "retinol acetylating enzyme", "enzyme having retinol acetylating activity" or "ATE" are used interchangeably herein and refer to enzymes [EC 2.3.1.84] which are capable of catalyzing the conversion of retinol into retinyl acetate with an amount of at least 80%, about 87, 90, 92, 95, 97, 99 or up to 100% of produced retinyl acetate in the trans-isoform. Said ATFs are capable of converting retinol, preferably trans-retinol, into retinyl ester, particularly retinyl acetate, with a total conversion of at least about 10%, preferably 12, 15, 20, 30, 40, 50, 80, 90 or even 100% (based on the total amount of retinoids within the retinoid mix produced by said host cell) towards generation of retinyl esters, e.g. retinyl acetate. A preferred isoform is ATF1.

The terms "conversion", "enzymatic conversion", "acetylation" or "enzymatic acetylation" in connection with enzymatic catalysis of retinol are used interchangeably herein and refer to the action of ATF, in particular Atf1 enzyme, as defined herein.

As used herein, the term "fungal host cell" includes particularly yeast as host cell, such as e.g. *Yarrowia* or *Saccharomyces*.

The ATF enzyme might be used in an isolated form (e.g. in a cell-free system) or might be expressed in a suitable host cell, such as e.g. a carotenoid-producing host cell, particularly fungal host cell. Enzymes might be expressed as endogenous enzymes or as heterologous enzymes. Preferably, the enzymes as described herein are introduced and expressed as heterologous enzymes in a suitable host cell, such as e.g. a carotenoid-producing host cell, particularly fungal host cell.

Suitable ATFs, particularly Atf1 enzymes, according to the present invention might be obtained from any source, such as e.g. plants, animals, including humans, algae, fungi, including yeast, or bacteria. Particular useful ATFs, preferably ATF1 enzymes, are obtained from yeast, in particular *Saccharomyces* or *Lachancea*, preferably obtained from *Saccharomyces bayanus*, such as e.g. SbATF1 (polypeptide sequence derived from AHX23958.1), *Lachancea mirantina* (LmATF1; SEQ ID NO:33), or *Lachancea fermentati* such as LfATF1 (polypeptide sequence derived from SCW02964.1) or LffATF1 polypeptide sequence derived from LT598487). Furthermore, particularly useful ATF1 enzymes are obtained from plants, including but not limited to plants selected from *Petunia, Euonymus, Malus,* or *Fragaria*, preferably obtained from *P. hybrida*, such as PhATF (polypeptide sequence derived from ABG75942.1), *E. alatus*, such as EaCAcT (polypeptide sequence derived from ADF57327.1), *M. domestica* (polypeptide sequence derived from AY517491) or *F. ananassa* (polypeptide sequence derived from AEM43830.1). Furthermore, particularly useful ATF1 enzymes are obtained from *Escherichia*, preferably *E. coli*, such as e.g. EcCAT (polypeptide sequence derived from EDS05563.1).

In one embodiment the polypeptides having ATF activity, particularly Atf1 enzyme activity, as defined herein, i.e. increased activity towards the formation of retinyl esters, particularly retinyl acetate, via acetylation of retinol, are obtainable from plants, such as *Petunia hybrida* (PhATF), in particular selected from polypeptides with at least about 60%, 70, 75, 80, 85, 90, 92, 95, 97, 98, 99% or up to 100% identity to polypeptide sequence derived from ABG75942.1, e.g. polypeptides with at least 60%, such as e.g. 70, 75, 85, 90, 92, 95, 97, 98, 99% or up to 100% identity to a polypeptide according to SEQ ID NO:11.

In one embodiment the polypeptides having ATF activity, particularly Atf1 enzyme activity, as defined herein, i.e. increased activity towards the formation of retinyl esters, particularly retinyl acetate, via acetylation of retinol, are obtainable from plants, such as *Euonymus alatus* (EaCAcT), in particular selected from polypeptides with at least about 60%, 70, 75, 80, 85, 90, 92, 95, 97, 98, 99% or up to 100% identity to a polypeptide sequence derived from ADF57327.1, said sequences being expressed in a suitable carotenoid-producing host cell and under suitable conditions as described herein, e.g. polypeptides with at least 60%, such as e.g. 65, 70, 80, 85, 90, 92, 95, 97, 98, 99% or up to 100% identity to a polypeptide according to SEQ ID NO:7.

In a further embodiment, the polypeptides having ATF activity, particularly Atf1 enzyme activity, as defined herein, i.e. increased activity towards the formation of retinyl esters, particularly retinyl acetate, via acetylation of retinol, are obtainable from bacteria, such as *E. coli* (EcCAT), in particular selected from polypeptides with at least about 60%, 65, 70, 75, 80, 85, 90, 92, 95, 97, 98, 99% or up to 100% identity to the polypeptide sequence derived from EDS05563.1, e.g. polypeptides with at least 60%, such as e.g. 65, 70, 75, 80, 85, 90, 92, 95, 97, 98, 99% or up to 100% identity to a polypeptide according to SEQ ID NO:5.

In one embodiment, the polypeptides having ATF activity, particularly Atf1 enzyme activity, as defined herein, i.e. increased activity towards the formation of retinyl esters, particularly retinyl acetate, via acetylation of retinol, are obtainable from yeast, such as *Saccharomyces bayanus* (SbATF1), in particular selected from polypeptides with at least about 60%, 65, 70, 75, 80, 85, 90, 92, 95, 97, 98, 99% or up to 100% identity to SEQ ID NO:1.

In another embodiment, the polypeptides having ATF activity, particularly Atf1 enzyme activity, as defined herein, i.e. increased activity towards the formation of retinyl esters, particularly retinyl acetate, via acetylation of retinol, are obtainable from yeast, such as *Lachancea mirantina* (LmATF1), in particular selected from polypeptides with at least about 60%, 65, 70, 75, 80, 85, 90, 92, 95, 97, 98, 99% or up to 100% identity to SEQ ID NO:13.

In yet another embodiment, the polypeptides having ATF activity, particularly Atf1 enzyme activity, as defined herein, i.e. increased activity towards the formation of retinyl esters, particularly retinyl acetate, via acetylation of retinol, are obtainable from yeast, such as *Lachancea fermentati*, in particular selected from polypeptides with at least about 60%, 65, 70, 75, 80, 85, 90, 92, 95, 97, 98, 99% or up to 100% identity to the polypeptide sequence derived from LT598487 or SCW02964.1, e.g. polypeptides with at least 60%, such as e.g. 65, 70, 75, 80, 85, 90, 92, 95, 97, 98, 99% or up to 100% identity to a polypeptide encoded by SEQ ID NO:16 or 18.

The host cell as described herein is capable of conversion of retinol into retinyl esters, particularly retinyl acetate, with a percentage of at least about 10%, preferably 12, 15, 20, 30, 40, 50, 80, 90 or even 100% towards production of retinyl esters. Preferably, such total conversion are obtained from a retinol mix comprising cis- and trans-retinol, with a percentage of at least about 65% as trans-retinol, such as e.g. at least about 68, 70, 75, 80, 85, 87, 90, 92, 95, 98, 99 or up to 100% retinol in trans-isoform, such as e.g. about 65 to 90% in trans-isoform, which is produced in the carotenoid-producing host cell, particularly a fungal host cell.

Preferably, the carotenoid-producing host cell, particularly fungal host cell, producing such high amount of trans-retinol as described herein is the same as the host cell converting the resulting retinol into retinyl esters, e.g. retinyl acetate, with a total conversion of at least about 10% towards retinyl esters. Preferably, the retinol mix to be converted into retinyl esters, particularly retinyl acetate, by the action of the ATF, particularly Atf1, as defined herein comprises at least 65% trans-retinol, such as e.g. about 65 to 90% in trans-isoform, resulting in a percentage of at least 65% trans-retinyl esters in the retinyl ester mix.

Thus, in one embodiment the invention is directed to a carotenoid-producing host cell, particularly fungal host cell, comprising a mix of cis- and trans-retinol with a percentage of at least 65% trans-retinol in the retinol mix, said retinol mix being converted by specific ATFs, particularly Atf1, as defined herein catalyzing the conversion of retinol, preferably trans-retinol, into retinyl esters, e.g. retinyl acetate, with a conversion rate of at least 10% towards retinyl esters, particularly retinyl acetate, which will have a percentage of at least 65% of trans-retinyl esters, e.g. trans-retinyl acetate.

Modifications in order to have the host cell as defined herein produce more copies of genes and/or proteins, such as e.g. ATFs with selectivity towards formation of retinyl esters, particularly retinyl acetate, preferably with at least 65% of the esters being in trans-isoform, may include the use of strong promoters, suitable transcriptional- and/or translational enhancers, or the introduction of one or more gene copies into the carotenoid-producing host cell, particularly fungal host cell, leading to increased accumulation of the respective enzymes in a given time. The skilled person knows which techniques to use depending on the host cell. The increase or reduction of gene expression can be measured by various methods, such as e.g. Northern, Southern or Western blot technology as known in the art.

The generation of a mutation into nucleic acids or amino acids, i.e. mutagenesis, may be performed in different ways, such as for instance by random or side-directed mutagenesis, physical damage caused by agents such as for instance radiation, chemical treatment, or insertion of a genetic element. The skilled person knows how to introduce mutations.

Thus, the present invention is directed to a carotenoid-producing host cell, particularly fungal host cell, as described herein comprising an expression vector or a polynucleotide encoding ATFs, particularly Atf1 enzymes, as described herein which has been integrated in the chromosomal DNA of the host cell. Such carotenoid-producing host cell, particularly fungal host cell, comprising a heterologous polynucleotide either on an expression vector or integrated into the chromosomal DNA encoding ATFs, particularly Atf1 enzymes, as described herein is called a recombinant host cell. The carotenoid-producing host cell, particularly fungal host cell, might contain one or more copies of a gene encoding the ATFs, particularly Atf1 enzymes, as defined herein, such as e.g. polynucleotides encoding polypeptides with at least about 60% identity to SEQ ID NOs:1, 3, 5, 7, 9, 11, 13, 16 or 18, leading to overexpression of such genes encoding the ATFs, particularly Atf1 enzymes, as defined herein. The increase of gene expression can be measured by various methods, such as e.g. Northern, Southern or Western blot technology as known in the art.

Based on the sequences as disclosed herein and on the preference for acetylation of retinol (preferably in the trans-isoform), into retinyl esters (preferably in the trans-isoform), particularly retinyl acetate, with a total conversion of at least about 10% obtained as retinyl esters, e.g. retinyl acetate, one could easily deduce further suitable genes encoding polypeptides having retinol acetylating activity as defined herein which could be used for the conversion of retinol into retinyl esters, particularly retinyl acetate. Thus, the present invention is directed to a method for identification of novel acetylating enzymes, wherein a polypeptide with at least 60%, such as e.g. 65, 70, 75, 80, 85, 90, 92, 95, 97, 98, 99% or up to 100% identity to known sequences, such as SEQ ID NOs:1, 3, 5, 7, 9, 11, 13, 16 or 18, is used as a probe in a screening process for new AFT enzymes, particular Atf1 enzymes, with preference for production of retinyl esters, particularly retinyl acetate, from conversion of retinol, wherein preferably the retinol comprises at least about 65% of retinol as trans-retinol. Any polypeptide having ATF, such as particularly Atf1, activity and disclosed herein might be used for production of retinyl esters, particularly retinyl acetates from retinol as described herein, as long as the acetylating action results in at least about 10% retinyl esters, particularly retinyl acetate, based on the total amount of produced retinoids.

The present invention is particularly directed to the use of such novel ATFs, particularly Atf1 enzymes, in a process for production of retinyl esters, particularly retinyl acetate, wherein the production of retinol LC-acyl is reduced. The process might be performed with a suitable carotenoid-producing host cell, particularly fungal host cell, expressing said ATF, particularly Atf1 enzyme, preferably wherein the genes encoding said enzymes are heterologous expressed, i.e. introduced into said host cells. Retinyl esters, in particular retinyl acetate, can be further converted into vitamin A by the action of (known) suitable chemical or biotechnological mechanisms.

Thus, the present invention is directed to a process for production of a retinyl ester mix comprising retinyl acetate, preferably with a percentage of at least 65% a trans-retinyl acetate, via enzymatic activity of one of the Atf1 enzymes as defined herein, comprising contacting retinol, preferably trans-retinol or a retinol mix with at least 65-90% in trans-isoform, with said Atf1 enzyme. Particularly, the invention is directed to a process for production of vitamin A, said process comprising (a) introducing a nucleic acid molecule encoding one of the Atf1 enzymes as defined herein into a suitable carotenoid-producing host cell, particularly fungal host cell, as defined herein, (b) enzymatic conversion, i.e. acetylation, of retinol, preferably with a percentage of at least 65-90% of trans-retinol, via action of said expressed Atf1 into a mix of trans- and cis-retinyl acetate, and (3) conversion of said retinyl acetate into vitamin A under suitable conditions known to the skilled person.

The terms "sequence identity", "% identity" are used interchangeable herein. For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity. With regards to enzymes originated from plants as defined herein, the skilled person is aware of the fact that plant-derived enzymes might contain a chloroplast targeting signal which is to be cleaved via specific enzymes, such as e.g. chloroplast processing enzymes (CPEs).

The ATFs, particularly Atf1 enzymes, as defined herein also encompasses enzymes carrying amino acid substitution(s) which do not alter enzyme activity, i.e. which show the same properties with respect to the wild-type enzyme and catalyze the conversion of retinol to retinyl esters, particularly retinyl acetate, wherein at least about 10% of retinol, such as e.g. a retinol-mix comprising at least 65% trans-retinol, is converted into retinyl esters, particularly retinyl acetate. Such mutations are also called "silent mutations", which do not alter the (enzymatic) activity of the enzymes as described herein.

A nucleic acid molecule according to the invention may comprise only a portion or a fragment of the nucleic acid sequence encoding polypeptides as defined herein, for example a fragment which may be used as a probe or primer or a fragment encoding a portion of ATF, particularly ATF1, as defined herein. The nucleotide sequence determined from the cloning of the ATF gene, particularly ATF1 gene, allows for the generation of probes and primers designed for use in identifying and/or cloning other homologues from other species. The probe/primer typically comprises substantially purified oligonucleotides which typically comprise a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence as disclosed herein, or fragments or derivatives thereof.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include, for example, 2 h to 4 days incubation at 42° C. using a digoxigenin (DIG)-labeled DNA probe (prepared by using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

Expression of the enzymes/polynucleotides encoding one of the specific ATFs, particularly Atf1 enzymes, as defined herein can be achieved in any host system, including (micro)organisms, which is suitable for carotenoid/retinoid production and which allows expression of the nucleic acids encoding one of the enzymes as disclosed herein, including functional equivalents or derivatives as described herein. Examples of suitable carotenoid/retinoid-producing host (micro)organisms are bacteria, algae, fungi, including yeasts, plant or animal cells. Preferred bacteria are those of the genera *Escherichia*, such as, for example, *Escherichia coli*, *Streptomyces*, *Pantoea* (*Erwinia*), *Bacillus*, *Flavobacterium*, *Synechococcus*, *Lactobacillus*, *Corynebacterium*, *Micrococcus*, *Mixococcus*, *Brevibacterium*, *Bradyrhizobium*, *Gordonia*, *Dietzia*, *Muricauda*, *Sphingomonas*, *Synochocystis*, *Paracoccus*, such as, for example, *Paracoccus zeaxanthinifaciens*. Preferred eukaryotic microorganisms, in particular fungi including yeast, are selected from *Saccharomyces*, such as *Saccharomyces cerevisiae*, *Aspergillus*, such as *Aspergillus niger*, *Pichia*, such as *Pichia pastoris*, *Hansenula*, such as *Hansenula polymorphs*, *Phycomyces*, such as *Phycomyces blakesleanus*, *Mucor*, *Rhodotorula*, *Sporobolomyces*, *Xanthophyllomyces*, *Phaffia*, *Blakeslea*, such as e.g. Blakeslea trispora, or *Yarrowia*, such as *Yarrowia lipolytica*. In particularly preferred is expression in a fungal host cell, such as e.g. *Yarrowia* or *Saccharomyces*, or expression in *Escherichia*, more preferably expression in *Yarrowia lipolytica* or *Saccharomyces cerevisiae*.

Depending on the host cell the polynucleotides as defined herein for acetylation of retinol might be optimized for expression in the respective host cell. The skilled person knows how to generate such modified polynucleotides. It is understood that the polynucleotides as defined herein also encompass such host-optimized nucleic acid molecules as long as they still express the polypeptide with the respective activities as defined herein.

Thus, in one embodiment, the present invention is directed to a carotenoid-producing host cell, particularly fungal host cell, comprising polynucleotides encoding ATFs, in particular Atf1 enzymes, as defined herein which are optimized for expression in said host cell, with no impact on growth of expression pattern of the host cell or the enzymes. Particularly, a carotenoid-producing host cell, particularly fungal host cell, is selected from yeast, e.g. *Yarrowia* or *Saccharomyces*, such as e.g. *Saccharomyces cerevisiae* or *Yarrowia lipolytica*, wherein the polynucleotides encoding the ATFs, particularly Atf1 enzymes, as defined herein are selected from polynucleotides with at least 60%, such as e.g. 65, 70, 75, 80, 85, 90, 92, 95, 97, 98, 99% or up to 100% identity to SEQ ID NOs:2, 4, 6, 8, 10, 12, 15, 17, or 19.

With regards to the present invention, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code). Thus, for example, strain *Lachancea mirantina* is a synonym of strain *Zygosaccharomyces* sp. IFO 11066, originated from Japan.

The present invention is directed to a process for production of retinyl esters, particularly retinyl acetate, to be used as e.g. building blocks in the production of vitamin A, wherein the retinyl esters are generated via acetylation of retinol (particularly comprising at least 65% of retinyl esters in trans-isoform obtained from conversion of retinol comprising at least 65% as trans-retinol) as disclosed herein by the action of ATF, particularly Atf1 enzymes, as described herein, wherein the acetylating enzymes are preferably heterologous expressed in a suitable host cell under suitable conditions as described herein. The produced retinyl esters, particularly retinyl acetate, might be isolated and optionally further purified from the medium and/or host cell. Said acetylated esters defined herein can be used as building blocks in a multi-step process leading to vitamin A. Vitamin A might be isolated and optionally further purified from the medium and/or host cell as known in the art.

Preferably, acetylation of retinol by the use of ATFs, particularly Atf1 enzymes, as described herein, leads to an increase of at least about 10%, such as e.g. 12, 15, 20, 30, 40, 50, 80, 90 or even 100% of acetylated retinoids, i.e. retinyl esters, present in the retinoid mix produced by the host cell. Preferred is the acetylation of trans-retinol into trans-retinyl esters by the action of the Atf1 enzymes as defined herein.

The host cell, i.e. microorganism, algae, fungal, animal or plant cell, which is capable of expressing the beta-carotene producing genes, the ATF genes, particularly ATF1 genes, as defined herein, optionally the genes encoding beta-carotene oxygenating enzymes, optionally the genes encoding retinal reducing enzymes and/or further genes required for biosynthesis of vitamin A, may be cultured in an aqueous medium supplemented with appropriate nutrients under aerobic or anaerobic conditions and as known by the skilled person for the respective carotenoid-producing host cells. Optionally, such cultivation is in the presence of proteins and/or co-factors involved in transfer of electrons, as known in the art. The cultivation/growth of the host cell may be conducted in batch, fed-batch, semi-continuous or continuous mode. Depending on the host cell, preferably, production of retinoids such as e.g. vitamin A and precursors thereof such as retinal, retinol, retinyl esters, can vary, as it is known to the skilled person. Cultivation and isolation of beta-carotene and retinoid-producing host cells selected from *Yarrowia* and *Saccharomyces* is described in e.g. WO2008042338. With regards to production of beta-carotene and retinoids in host cells selected from *E. coli*, methods are described in e.g. US20070166782.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in pmol substrate consumed or product formed per min per mg of protein. Typically, pmol/min is abbreviated by U (=unit). Therefore, the unit definitions for specific activity of pmol/min/(mg of protein) or U/(mg of protein) are used interchangeably throughout this document. An enzyme is active, if it performs its catalytic activity in vivo, i.e. within the host cell as defined herein or within a suitable (cell-free) system in the presence of a suitable substrate. The skilled person knows how to measure enzyme activity, Analytical methods to evaluate the capability of a suitable ATF, particularly Atf1, as defined herein for retinyl ester production, particularly retinyl acetate production, from conversion of retinol are known in the art, such as e.g. described in Example 4 of WO2014096992. In brief, titers of products such as retinyl esters, particularly retinyl acetate, retinol, trans-retinal, cis-retinal, beta-carotene and the like can be measured by HPLC.

As used herein, a "carotenoid-producing host cell" is a host cell, wherein the respective polypeptides are expressed and active in vivo leading to production of carotenoids, e.g. beta-carotene. The genes and methods to generate carotenoid-producing host cells are known in the art, see e.g. WO2006102342. Depending on the carotenoid to be produced, different genes might be involved.

As used herein, a "retinoid-producing host cell" is a host cell, wherein the respective polypeptides are expressed and active in vivo, leading to production of retinoids, e.g. vitamin A and its precursors, via enzymatic conversion of beta-carotene via retinal, retinol and retinyl esters. These polypeptides include the ATFs as defined herein. The genes of the vitamin A pathway and methods to generate retinoid-producing host cells are known in the art.

Retinoids as used herein include beta carotene cleavage products also known as apocarotenoids, including but not limited to retinal, retinolic acid, retinol, retinoic methoxide, retinyl acetate, retinyl esters, 4-keto-retinoids, 3 hydroxy-retinoids or combinations thereof. Long chain retinyl esters as used herein define hydrocarbon esters that consists of at least about 8, such as e.g. 9, 10, 12, 13, 15 or 20 carbon atoms and up to about 26, such as e.g. 25, 22, 21 or less carbon atoms, with preferably up to about 6 unsaturated bonds, such as e.g. 0, 1, 2, 4, 5, 6 unsaturated bonds. Long chain retinyl esters include but are not limited to linoleic acid, oleic acid or palmitic acid. Biosynthesis of retinoids is described in e.g. WO2008042338.

"Retinal" as used herein is known under IUPAC name (2E,4E,6E,8E)-3,7-Dimethyl-9-(2,6,6-trimethylcyclohexen-1-yl)nona-2,4,6,8-tetraenal. It is herein interchangeably referred to as retinaldehyde or vitamin A aldehyde and includes both cis- and trans-isoforms, such as e.g. 11-cis retinal, 13-cis retinal, trans-retinal and all-trans retinal.

The term "carotenoids" as used herein is well known in the art. It includes long, 40 carbon conjugated isoprenoid polyenes that are formed in nature by the ligation of two 20 carbon geranylgeranyl pyrophosphate molecules. These include but are not limited to phytoene, lycopene, and carotene, such as e.g. beta-carotene, which can be oxidized on the 4-keto position or 3-hydroxy position to yield canthaxanthin, zeaxanthin, or astaxanthin. Biosynthesis of carotenoids is described in e.g. WO2006102342.

"Vitamin A" as used herein may be any chemical form of vitamin A found in aqueous solutions, such as for instance undissociated, in its free acid form or dissociated as an anion. The term as used herein includes all precursors or intermediates in the biotechnological vitamin A pathway. It also includes vitamin A acetate.

The retinyl esters as described herein are present in the form of a "retinyl-ester mix" comprising preferably acetylated forms, including retinyl acetate and/or other esters, such as long chain retinyl esters. Preferably, the retinyl ester mix comprises at least about 65%, such as e.g. 70, 75, 80, 90, 92, 95, 97, 99 or up to 100% of retinyl esters being acetates, i.e. retinyl acetates.

The term "long chain retinyl ester" defines hydrocarbon esters that consists of at least about 8, such as e.g. 9, 10, 12, 13, 15 or 20 carbon atoms and up to about 26, such as e.g. 25, 22, 21 or less carbon atoms, with preferably up to about 6 unsaturated bonds, such as e.g. 0, 1, 2, 4, 5, 6 unsaturated bonds. Long chain retinyl esters include but are not limited to retinyl-linolate, retinyl-oleate or retinyl palmitate.

The present invention particularly features the following embodiments (1) to (17):

(1) A carotenoid-producing host cell, particularly fungal host cell, comprising an enzyme with acetylating activity, such as retinol acetylating activity, preferably acetyl transferase (ATF) [EC 2.3.1.84], more preferably an enzyme with acetyl transferase 1 (Atf1) activity, said enzyme catalyzing the conversion of retinol, preferably trans-retinol, to a retinyl acetate mix, with a percentage of at least 10% of acetylated retinol, i.e. retinyl acetate, based on the total amount of retinoids produced by said host cell.

(2) A carotenoid-producing host cell, particularly fungal host cell, comprising an enzyme with retinol acetylating activity, preferably acetyl transferase [EC 2.3.1.84] activity, more preferably acetyl transferase 1 activity, said host cell producing a retinyl ester mix comprising retinyl acetate, wherein the mix comprises at least about 65%, preferably 80, 87, 90, 92, 95, 97, 99 or up to 100% retinyl esters in trans-isoform.

(3) The carotenoid-producing host cell, particularly fungal host cell, of embodiment (1) or (2), wherein the retinyl ester is selected from retinyl acetate.

(4) The carotenoid-producing host cell, particularly fungal host cell, of embodiment (1), (2) or (3) comprising a heterologous acetyl transferase, preferably heterologous acetyl transferase 1.

(5) The carotenoid-producing host cell of embodiments (1), (2), (3) or (4), wherein the acetyl transferase, preferably acetyl transferase 1, is selected from plants, animals, including humans, algae, fungi, including yeast or bacteria, preferably selected from *Saccharomyces, Fragaria, Escherichia, Euonymus, Malus, Petunia* or *Lachancea*.

(6) The carotenoid-producing host cell of embodiment (5), wherein the acetyl transferase is acetyl transferase 1 selected from *Saccharomyces bayanus, Fragaria ananassa, Escherichia coli, Euonymus alatus, Malus domestica, Petunia hybrida, Lachancea mirantina* or *Lachancea fermentati*.

(7) The carotenoid-producing host cell, particularly fungal host cell, of embodiment (6), wherein the acetyl transferase 1 is selected from a polypeptide with at least 60% identity to a polypeptide according to SEQ ID NOs:1, 3, 5, 7, 9, 11, 13, 16 or 18.

(8) The carotenoid-producing host cell of embodiments (1), (2), (3), (4), (5), (6) or (7), wherein the host cell is selected from plants, fungi, algae or microorganisms, preferably selected from fungi including yeast, more preferably from *Saccharomyces, Aspergillus, Pichia, Hansenula, Phy-*

*comyces, Mucor, Rhodotorula, Sporobolomyces, Xanthophyllomyces, Phaffia, Blakeslea* or *Yarrowia*, even more preferably from *Yarrowia lipolytica* or *Saccharomyces cerevisiae*.

(9) The carotenoid-producing host cell of embodiments (1), (2), (3), (4), (5), (6) or (7), wherein the host cell is selected from plants, fungi, algae or microorganisms, preferably selected from *Escherichia, Streptomyces, Pantoea, Bacillus, Flavobacterium, Synechococcus, Lactobacillus, Corynebacterium, Micrococcus, Mixococcus, Brevibacterium, Bradyrhizobium, Gordonia, Dietzia, Muricauda, Sphingomonas, Synochocystis* or *Paracoccus*.

(10) The carotenoid-producing host cell, particularly fungal host cell, of embodiment (1), (2), (3), (4), (5), (6), (7), (8) or (9), wherein the retinyl ester comprising retinyl acetate is further converted into vitamin A.

(11) A process for production of a retinyl ester mix comprising retinyl acetate via enzymatic activity of acetyl transferase [EC 2.3.1.84], preferably activity of acetyl transferase 1, comprising contacting retinol with said acetyl transferase, preferably acetyl transferase 1, wherein at least about 65 to 90% of retinol is in trans-isoform.

(12) A process of embodiment (11) using the carotenoid-producing host cell, particularly fungal host cell, of embodiments (1), (2), (3), (4), (5), (6), (7), (8), (9) or (10).

(13) A process for production of vitamin A comprising the steps of:
(a) introducing a nucleic acid molecule encoding acetyl transferase [EC 2.3.1.84] as defined herein into a suitable carotenoid-producing host cell, preferably carotenoid-producing host cell, particularly fungal host cell, of embodiment (1), (2), (3), (4), (5), (6), (7), (8) or (9);
(b) enzymatic conversion of retinol comprising trans- and cis-retinol with at least about 65 to 90% as trans-retinol into a retinyl acetate mix comprising cis- and trans-retinyl acetate,
(c) conversion of retinyl acetate into vitamin A under suitable culture conditions.

(14) Use of acetyl transferase [EC 2.3.1.84] as above and defined herein for production of a retinyl acetate mix comprising trans- and cis-retinyl acetate, wherein at least about 65 to 90% of acetates are in trans-isoform, wherein the acetyl transferase is heterologous expressed in the carotenoid-producing host cell, particularly fungal host cell, of embodiments (1), (2), (3), (4), (5), (6), (7), (8), (9) or (10), said retinyl acetate mix being obtained via conversion of a retinol mix comprising trans- and cis-retinol, wherein at least about 65 to 90% of retinols are in trans-isoform.

(15) A process for production of a retinyl ester mix comprising retinyl acetate via enzymatic activity of acetyl transferase [EC 2.3.1.84], preferably activity of acetyl transferase 1, comprising contacting retinol with said acetyl transferase, preferably acetyl transferase 1, wherein the ratio of trans- to cis-isoforms in the mix is at least about 4.

(16) A process for production of vitamin A comprising the steps of:
(a) introducing a nucleic acid molecule encoding acetyl transferase [EC 2.3.1.84] into a suitable carotenoid-producing host cell,
(b) enzymatic conversion of retinol into a retinyl acetate mix comprising trans- and cis-retinyl acetate in a ratio of at least about 4:1,
(c) conversion of retinol into vitamin A under suitable culture conditions.

(17) Use of acetyl transferase [EC 2.3.1.84] for production of a retinyl acetate mix comprising trans- and cis-retinyl acetate in a ratio of at least about 4:1, wherein the acetyl transferase is heterologous expressed in a suitable carotenoid-producing host cell.

The following examples are illustrative only and are not intended to limit the scope of the invention in any way. The contents of all references, patent applications, patents, and published patent applications, cited throughout this application are hereby incorporated by reference, in particular WO2008042338, WO2014096992, WO2016172282, WO2009126890, US20070166782 or US20160130628.

EXAMPLES

Example 1: General Methods, Strains, and Plasmids

All basic molecular biology and DNA manipulation procedures described herein are generally performed according to Sambrook et al. (eds.), Molecular Cloning: A Laboratory Manual. Cold Spring Harbor Laboratory Press: New York (1989) or Ausubel et al. (eds). Current Protocols in Molecular Biology. Wiley: New York (1998).

Shake Plate Assay.

Typically, 800 µl of 0.25% Yeast extract, 0.5% peptone (0.25X YP) is inoculated with 10 µl of freshly grown *Yarrowia* and overlaid with 800 µl of mineral oil (Drakeol 5, Penreco Personal Care Products, Karns City, PA, USA) carbon source 5% corn oil in mineral oil and/or 5% in glucose in aqueous phase. Transformants were grown in 24 well plates (Microplate Devices 24 Deep Well Plates Whatman 7701-5102), covered with mat seal (Analytical Sales and Services Inc. Plate Mats 24010CM), sterile sealed with Qiagen Airpore Tape Sheets (19571) and shaken in Infors multi plate shaker (Multitron), 30° C., 800 RPM in YPD media with for 4 days. The mineral oil fraction was removed from the shake plate wells and analyzed by HPLC on a normal phase column, with a photo-diode array detector. This method is used in Examples 2, 3, 4.

DNA Transformation.

Strains are transformed by overnight growth on YPD plate media. 50 µl of cells is scraped from a plate and transformed by incubation in 500 µl with 1 µg transforming DNA, typically linear DNA for integrative transformation, 40% PEG 3550MW, 100 mM lithium acetate, 50 mM Dithiothreitol, 5 mM Tris-Cl pH 8.0, 0.5 mM EDTA for 60 minutes at 40° C. and plated directly to selective media or in the case of dominant antibiotic marker selection the cells are out grown on YPD liquid media for 4 hours at 30° C. before plating on the selective media.

DNA Molecular Biology.

Genes were synthesized with NheI and MluI ends in pUC57 vector (GenScript, Piscataway, NJ). Typically, the genes were subcloned to the MB5082 'URA3', MB6157 HygR, and MB8327 NatR vectors for marker selection in *Yarrowia lipolytica* transformations, as in WO2016172282. For clean gene insertion by random nonhomologous end joining of the gene and marker HindIII/XbaI (MB5082) or PvuII (MB6157 and MB8327), respectively purified by gel electrophoresis and Qiagen gel purification column. MB5082 'URA3' marker could be reused due to gratuitous repeated flanking sequences that enable selection of circular excisants of the URA3 cassette on FOA. The NatR and HygR markers can be removed by transient expression of Cre recombinase that results in excisants due to the flanking Lox sites.

Plasmid List.

Plasmid, strains, nucleotide and amino acid sequences to be used are listed in Table 1, 2 and the sequence listing.

Nucleotide sequence ID NOs:2, 4, 6, 8, 10, 12, 15, 17 and 19 are codon optimized for expression in *Yarrowia*.

TABLE 1 list of plasmids used for construction of the strains carrying the heterologous ATF1-genes. The sequence ID NOs refer to the inserts. For more details, see text.

| MB plasmid | Backbone MB | Insert | SEQ ID NO: (aa/nt) |
|---|---|---|---|
| 8064 | 5082 | SbATF1 | 1/2 |
| 8509 | 6157 | FaATF | 3/4 |
| 8510 | 6157 | EcCAT | 5/6 |
| 8511 | 6157 | EaCAcT | 7/8 |
| 8512 | 6157 | MdATF | 9/10 |
| 8513 | 6157 | PhATF | 11/12 |
| 8849 | 5082 | LmATF1 | 13/55 |
| 8610 | 5082 | LfATF1 | 16/17 |
| 8806 | 5082 | LffATF1 | 18/19 |

TABLE 2 list of *Yarrowia* strains used for production of retinoids carrying the heterologous ATF1 genes. For more details, see text.

| ML strain | Description | First described in |
|---|---|---|
| 7788 | Carotene strain | WO2016172282 |
| 15710 | ML7788 transformed with MB7311 -Mucor CarG | WO2016172282 |
| 17544 | ML15710 cured of URA3 by FOA and HygR by Cre/lox | here |
| 17767 | ML17544 transformed with MB6072 DmBC0-URA3 and MB6732 SbATF1-HygR and cured of markers | here |
| 17978 | ML17968 transformed with MB8200 FfRDH-URA3 and cured of markers | here |

Normal Phase Retinol Method.

A Waters 1525 binary pump attached to a Waters 717 auto sampler were used to inject samples. A Phenomenex Luna 3p Silica (2), 150×4.6 mm with a security silica guard column kit was used to resolve retinoids. The mobile phase consists of either, 1000 mL hexane, 30 mL isopropanol, and 0.1 mL acetic acid for astaxanthin related compounds, or 1000 mL hexane, 60 mL isopropanol, and 0.1 mL acetic acid for zeaxanthin related compounds. The flow rate for each is 0.6 mL per minute. Column temperature is ambient. The injection volume is 20 µL. The detector is a photodiode array detector collecting from 210 to 600 nm. Analytes were detected according to Table 3.

TABLE 3 list of analytes using normal phase retinol method. The addition of all added intermediates gives the amount of total retinoids. For more details, see text.

| Intermediates | Retention time [min] | Lambda max [nm] |
|---|---|---|
| 11-cis-dihydro-retinol | 7.1 | 293 |
| 11-cis-retinal | 4.0 | 364 |
| 11-cis-retinol | 8.6 | 318 |
| 13-cis-retinal | 4.1 | 364 |
| dihydro-retinol | 9.2 | 292 |
| retinyl-acetate | 3.5 | 326 |
| retinyl-ester | 3 | 325 |
| trans-retinal | 4.7 | 376 |
| trans-retinol | 10.5 | 325 |

Sample Preparation.

Samples were prepared by various methods depending on the conditions. For whole broth or washed broth samples the broth was placed in a Precellys® tube weighed and mobile phase was added, the samples were processed in a Precellys® homogenizer (Bertin Corp, Rockville, MD, USA) on the highest setting 3× according to the manufactures directions. In the washed broth the samples were spun in a 1.7 ml tube in a microfuge at 10000 rpm for 1 minute, the broth decanted, 1 ml water added mixed pelleted and decanted and brought up to the original volume. The mixture was pelleted again and brought up in appropriate amount of mobile phase and processed by Precellys® bead beating. For analysis of mineral oil fraction, the sample was spun at 4000 RPM for 10 minutes and the oil was decanted off the top by positive displacement pipet (Eppendorf, Hauppauge, NY, USA) and diluted into mobile phase mixed by vortexing and measured for retinoid concentration by HPLC analysis.

Fermentation Conditions.

Fermentations were identical to the previously described conditions using preferably a silicone oil or a mineral oil overlay and stirred tank that was preferably glucose or corn oil fed in a bench top reactor with 0.5 L to 5 L total volume (see WO2016172282). Generally, the same results were observed with a fed batch stirred tank reactor with an increased productivity demonstrating the utility of the system for the production of retinoids. Preferably, fermentations were batched with 5% glucose and 20% silicone oil was added after dissolved oxygen plummeted and feed was resumed to achieve 20% dissolved oxygen throughout the feeding program. Alternatively, corn oil was used as a feed and mineral oil was used as a second phase to collect the aliphatic retinoids.

Example 2: Production of Retinoids in *Yarrowia lipolytica*

For expression of heterologous ATF1, the trans retinol producing strain ML17968 was transformed with purified PvuII gene fragments containing acetyl-transferase gene fragments linked to a Hygromycin resistance marker (HygR) for selection on rich media (YPD) containing 100 ug/nnl hygromycin. Prior to plating the cultures were outgrown in YPD for four hours to synthesize the antibiotic resistance genes. Isolates were screened for acylation in shake plate assays, specifically using 10% glucose as a carbon source in 0.25X YP with silicone oil as an overlay and successful isolates were further screened in fed batch stirred tank reactor with glucose feed and silicone oil overlay, which showed an order of magnitude increased productivity indicating utility in the production of retinoids. The data from the analysis are shown in Table 4).

TABLE 4 trans-retinoid production in *Yarrowia* as enhanced by action of heterologous Atf1 enzymes. Analysis was done in a shake plate fermentation "% trans" means percentage of trans-retinyl acetate in the mix of retinoids, and analysis was done in shake plates (SP) and fed batch stirred tanks (ST). "n.a." means not available. For more details, see text.

| Organism | ATF1 gene | % acetylation- | ML strain | MB plasmid |
|---|---|---|---|---|
| S. bayanus | SbATF1 | 10.3 | 17968 | 6832 |
| P. hybrida | PhATF | 2.1 | 17968 | 8513 |
| E. alatus | EaCAcT | 0.45 | 17968 | 8511 |
| E. coli | EcCAT | 0.35 | 17968 | 8510 |
| L. mirantina | LfATF1 | 9.6 | 18523 | 8610 |
| L. fermentata | LffATF1 | 11.7 | 18523 | 8806 |
| L. fermentata | LmATF1 | 40.4 | 18523 | 8849 |

Example 3: Production of Retinoids in *Saccharomyces cerevisiae*

Typically, a beta carotene strain is transformed with heterologous genes encoding for enzymes such as geranylgeranyl synthase, phytoene synthase, lycopene synthase, lycopene cyclase constructed that is producing beta carotene according to standard methods as known in the art (such as e.g. as described in US20160130628 or WO2009126890). By introducing and/or overexpressing the ATF enzymes as defined herein, similar results regarding production of retinyl acetate, in particular with at least 60% in trans-isoform, are obtained. Further, when transformed with beta carotene oxidase genes retinal can be produced. Further, when transformed with retinol dehydrogenase, then retinol can be produced. Optionally, the endogenous retinol acylating genes can be deleted. With this approach, similar results regarding specificity for trans-isoform or productivity towards retinyl acetate are obtained.

The invention claimed is:

1. A retinol-producing host cell expressing a heterologous acetyl transferase 1 enzyme comprising an amino acid sequence having at least 90% identity to SEQ ID NO: 13, wherein the host cell is a recombinant *Yarrowia lipolytica* or *Saccharomyces cerevisiae* capable of producing a mix of retinoids comprising at least 40% acetylated retinol.

2. The retinol-producing host cell according to claim 1, wherein the heterologous acetyl transferase 1 enzyme comprises an amino acid sequence having at least 95% identity to SEQ ID NO: 13.

3. The retinol-producing host cell according to claim 1, wherein the heterologous acetyl transferase 1 enzyme comprises the amino acid sequence of SEQ ID NO: 13.

4. The retinol-producing host cell according to claim 1, wherein the heterologous acetyl transferase 1 enzyme is a *L. mirantina* acetyl transferase 1.

* * * * *